(12) United States Patent
Bishop

(10) Patent No.: US 9,398,845 B2
(45) Date of Patent: Jul. 26, 2016

(54) METHOD AND APPARATUS FOR DETERMINING EYE TOPOLOGY

(71) Applicant: Eyedeal Scanning, LLC., Needham, MA (US)

(72) Inventor: Robert P Bishop, Newton, MA (US)

(73) Assignee: EYEDEAL SCANNING LLC, Needham, MA (US)

( * ) Notice: Subject to any disclaimer, the term of this patent is extended or adjusted under 35 U.S.C. 154(b) by 171 days.

(21) Appl. No.: 13/654,151

(22) Filed: Oct. 17, 2012

(65) Prior Publication Data

US 2013/0093998 A1 Apr. 18, 2013

Related U.S. Application Data

(60) Provisional application No. 61/547,904, filed on Oct. 17, 2011.

(51) Int. Cl.

| | |
|---|---|
| *A61B 3/10* | (2006.01) |
| *A61B 3/107* | (2006.01) |
| *A61B 3/113* | (2006.01) |
| *A61B 3/14* | (2006.01) |
| *A61B 3/15* | (2006.01) |

(52) U.S. Cl.
CPC ............... *A61B 3/102* (2013.01); *A61B 3/107* (2013.01); *A61B 3/113* (2013.01); *A61B 3/145* (2013.01); *A61B 3/152* (2013.01)

(58) Field of Classification Search
CPC ........ A61B 3/102; A61B 3/107; A61B 3/113; A61B 3/14; A61B 3/145; A61B 3/15; A61B 3/152
USPC .................................................. 351/206–212
See application file for complete search history.

(56) References Cited

U.S. PATENT DOCUMENTS

| | | | | |
|---|---|---|---|---|
| 4,582,404 | A * | 4/1986 | Hamilton | ............... A61B 3/107 351/212 |
| 4,761,071 | A * | 8/1988 | Baron | ........................... 351/212 |
| 5,321,501 | A | 6/1994 | Swanson et al. | |
| 5,493,109 | A | 2/1996 | Wei et al. | |
| 5,512,965 | A | 4/1996 | Snook | |
| 6,741,359 | B2 | 5/2004 | Wei et al. | |
| 7,237,898 | B1 | 7/2007 | Hohla et al. | |
| 2006/0158612 | A1 | 7/2006 | Polland et al. | |
| 2006/0210122 | A1 | 9/2006 | Cleveland et al. | |
| 2009/0190093 | A1* | 7/2009 | Tanassi | .................. A61B 3/117 351/208 |
| 2011/0037942 | A1 | 2/2011 | Lieberman et al. | |
| 2012/0182522 | A1* | 7/2012 | Frey | ......................... A61B 3/14 351/206 |

FOREIGN PATENT DOCUMENTS

| | | |
|---|---|---|
| CN | 1553783 | 12/2004 |
| CN | 1604753 | 4/2005 |

OTHER PUBLICATIONS

PCT/US2012/060631 International Search Report and Written Opinion.

\* cited by examiner

*Primary Examiner* — Thomas K Pham
*Assistant Examiner* — Cara Rakowski
(74) *Attorney, Agent, or Firm* — Cesari and McKenna, LLP

(57) ABSTRACT

A method and apparatus for measuring the topography of the corneal and scleral regions of the eye. The measurements provide surface contours that are useful in the manufacture of scleral contact lenses.

18 Claims, 27 Drawing Sheets

METHOD AND APPARATUS FOR DETERMINING EYE TOPOLOGY

CROSS REFERENCE TO RELATED APPLICATIONS

This application claims the benefit of US Provisional Application No. 61/547,904, filed on Oct. 17, 2011. The contents of which is hereby incorporated by reference in its entirety.

BACKGROUND OF THE INVENTION

1. Field of the Invention

This invention generally relates to a method and apparatus for making optical measurements and more specifically to a method and apparatus for measuring the topography of an eye particularly over the regions of the cornea and sclera.

2. Description of Related Art

Accurate knowledge of the surface shape or "topography" of a patient's eye is essential to a number of ophthalmic procedures, examinations and diagnoses of the eye, such as cataract procedures, Lasik procedures and the manufacture of properly fitting, optically functional, comfortable contact lens. In all these applications information about the topography of the cornea and sclera is particularly important. In regions where a lens contacts the eye, including regions under the eyelids, precise knowledge of eye topology greatly facilitates manufacturing the lens in such a way as to achieve optimal rotational orientation and patient comfort. However, measuring eye topology, and more specifically that of the cornea and sclera, is complicated by the steep curvature of the eye in the scleral region, eyelid obstruction of the upper and lower scleral regions, and random eye motion during the measurement procedure.

Prior art apparatus incorporating Optical Coherent Tomography (OCT) and Placido Rings technology and currently used to measure eye topology have various limitations with respect to acquiring measurements that can be used to construct an accurate model of an individual's eye. Placido Ring technology, for example, operates by projecting a series of concentric rings onto the surface of the eye and measuring ring placement and distortion to determine surface topology. However, this technology does not provide sufficient and accurate information due to surface irregularities along the rotational axis of the projected ring. Consequently information can be lost if the rings merge together due to irregularities in eye surface topology. Resolution is limited in the radial direction due to a small number of rings, on the order of 22, and surface topology cannot be measured under the eyelids. OCT operates by acquiring a temporal series of height profile cross sections of the eye scanned at different angular positions around an axis normal to the front surface of the pupil. To create a three-dimensional model of the eye multiple cross sections must be scanned without the eye moving and then accurately combined maintaining strict alignment between the scanned cross sections. Unfortunately, if the eye moves during or between successive sequential cross sectional measurements, the model will be inaccurate, because there is no way to reference each cross section to a fixed spatial reference on the patient's eye. In addition, cross sections are currently limited to approximately 16 mm in diameter due to the steep curvature of the sclera. A 16 mm diameter image is insufficient to incorporate the wide scleral contact lenses with diameters up to 22 mm. Moreover, OCT and Placido Ring scanners are not readily adapted to measure scleral topology under an individual's eyelids.

U.S. Pat. No. 5,493,109 to Wei et al. (hereinafter "Wei-109") discloses OCT apparatus with an ophthalmologic surgical microscope. Automatic focusing is provided by driving a motorized internal focusing lens of the ophthalmologic surgical microscope with a signal output from the OCT apparatus. An embodiment of such a system includes: (a) optical coherence tomography apparatus; (b) a beam combiner for internally coupling output from the OCT apparatus into the ophthalmologic surgical microscope; and (c) a motor for moving an internal focusing lens of the ophthalmologic surgical microscope in response to a signal from the OCT apparatus.

U.S. Pat. No. 6,741,359 to Wei et al. (hereinafter "Wei-359") discloses OCT apparatus and describes the particular methodology and limitations of the system described in Wei-109. Wei-359 discloses one embodiment of a scanner for a beam of scanning OCT radiation that includes: (a) a source of OCT radiation; (b) a scanner; and (c) scanning optics in which an image surface has a negative field curvature. As disclosed, Wei-109 is limited to scanning the corneal region of the eye. This system utilizes a large aperture and auto-focusing to meet the depth of field parameters of the cornea. As a result, and as described later, this process also affects the light collection efficiency of the system. In Wei-359 custom optics focuses a beam of OCT radiation in a curved arc that approximates that of the human cornea. The object is to confine OCT radiation to be parallel to the surface of the eye. Such a system produces depth profile information along user-programmed radial scan lines that traverse the diameter of the eye. As a practical matter such a system appears limited to measurements of the corneal region and unable to cover the corneal and entire sclera regions.

Recently attempts have been made to manufacture "scleral lenses" for individuals whose corneas were damaged or deformed by accidents, such as explosions, or who are diagnosed with Keratoconus, a disease that causes the central area of the cornea to thin and bulge outward. As conventional contact lens sit on the corneal surface, they are not appropriate for such individuals. However, scleral contact lenses rest on the sclera and not the deformed cornea. Consequently such sclera lenses have been used to restore vision to many patients. The lens works by creating a new optical surface that is raised above the damaged cornea. The gap between the back of the lens and corneal surface fills with the patient's own tears creating a pool of liquid tears that act as a liquid bandage to soothe the nerves on the corneal surface. The newly formed rigid front optical surface of the lens then focuses light through the patient's eye onto the back retina to restore vision. To achieve the best optical performance with optimal patient comfort, the scleral lens must perfectly match the shape, curvature, and topology of the patient's sclera, which is the bearing surface of the lens including the bearing regions under the eyelids.

Prior art measurement apparatus, such as OCT apparatus, is not an optimal choice for making such measurements due to their limited scanning diameter and area. That is, such prior art measurement systems cannot reach sufficiently far into the sclera where the lens contacts the eye. Moreover, a human eye often has a toric shape so the long and short axes not necessarily at 0° and 90°. Toric eye profile information also needs to be computed to achieve optimal fit. Prior art systems do not measure the toricity of the sclera or provide the scan orientation of the long and short toric axes.

This lack of measurement capability has limited the use of sclera lens. Currently, it is necessary to manufacture a set of trial lenses to allow a physician to determine the most comfortable lens in the set, much like finding the best shoe size that fits a customer's foot without even having a ruler to first measure foot size. As will be apparent, fitting scleral lenses is very time consuming, can only be performed by a few specially trained doctors and trained personnel, requires skilled personnel at all phases and is very expensive.

SUMMARY

Therefore, it is an object of this invention to provide a method and apparatus for providing accurate measurements of the topography of the eye.

Another object of this invention is to provide a method and apparatus for providing accurate measurements of the topography of the corneal and scleral regions of the eye.

Still another object of this invention is to provide a method and apparatus for providing accurate measurements of the topography of the corneal and scleral regions of the eye that takes into account the toricity of the scleral region.

Yet another object of this invention is to provide a method and apparatus for minimizing and simplifying the effort for making scleral contact lenses.

Yet still another object of this invention is to provide a method and apparatus for minimizing and simplifying the process for determining the topography of the eye.

Still yet another object of this invention is to provide a method and apparatus for minimizing and simplifying the process for determining the topography of the corneal and sclera regions of an eye.

Yet still another object of this invention is to provide a method and apparatus for measuring the toricity of the sclera automatically, for computing the long and short toric axes automatically and for scanning the eye automatically to provide profile information along the two toric axes.

Yet still another object of this invention is to provide a method and apparatus for creating a three dimensional model of the eye in the scleral-corneal region.

In accordance with one aspect of this invention, an apparatus for measuring the topography of the surface of an eye characterized by at least one distinct visual feature includes a camera, a scanner and a control. The camera is aimed along an imaging axis for capturing a two-dimensional image of the eye's surface including at least one distinct visual feature. The scanner generates distance information corresponding to the distances from an internal reference to the surface of the eye at a plurality of positions along each of a plurality of spaced scan lines during a scanning operation. During this scanning, a fixed spatial relationship is maintained between the camera and the scanner. The control connects to the camera and the scanner. It functions to: (1) control the scanner to produce at least one scan along a scan line during a scanning operation thereby to obtain a plurality of distances at the along a scan line, (2) to cause the camera to capture at least one eye image during each scan, and (3) to store, for each scan, the distance information obtained by the scanner and the corresponding captured image information from the camera. A processing module combines the distance information from each scan line and the corresponding captured image information thereby to obtain an accurate representation of the topography of the eye.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
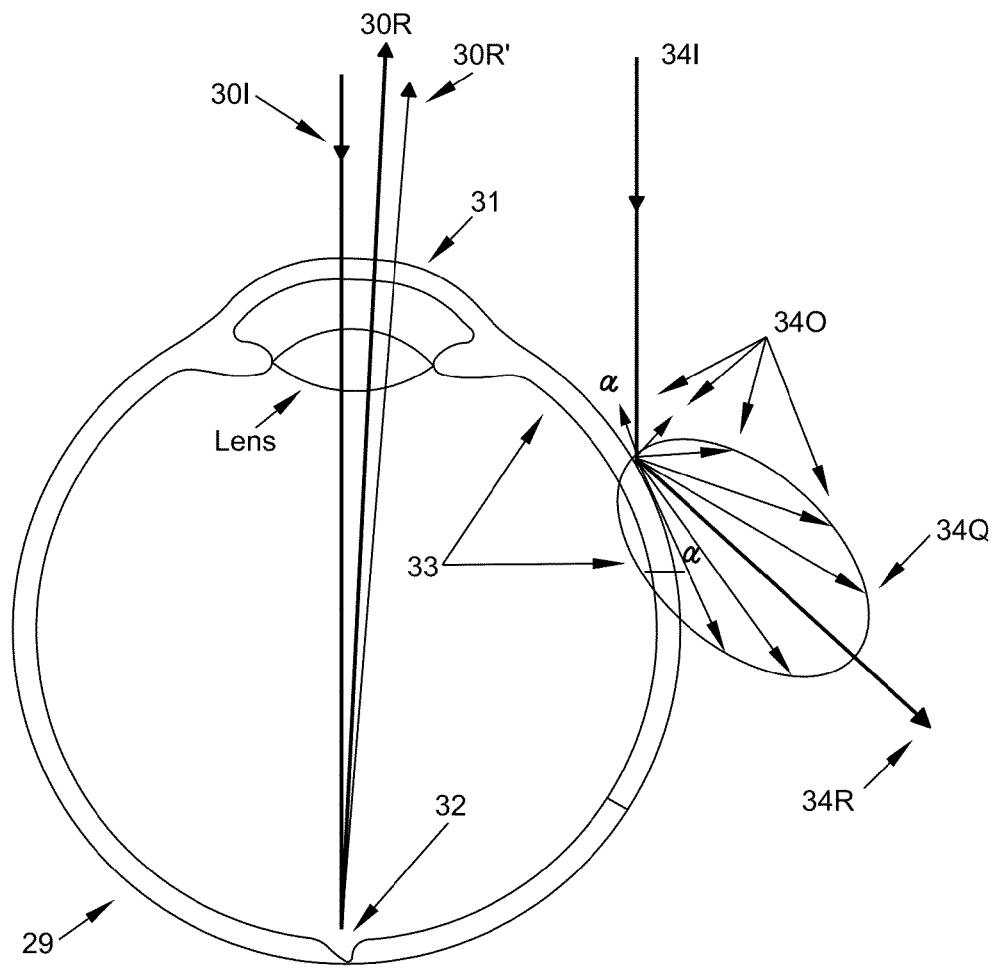
FIG. 1 depicts a simplified cross section of an eye.

FIGS. 1 through 6 are useful in understanding the prior art and the limitations of the prior art when applied to determining, with accuracy, the topography of the corneal and scleral regions of any eye, particularly when the information is to be used in the manufacture of scleral lenses. It is difficult to image surface regions, such as the sclera region of the eye with its steep curvature. FIG. 1 depicts an eye 29 in cross section. When an incident light beam 30I from a source impinges perpendicularly upon the surface of the cornea 31 and retina 32, it is reflected and scattered back toward the imaging optics as indicated by reflected light beams 30R and 30R'. However, when an incident light beam 34I impinges upon the steep area of the sclera 33, most light is reflected and scattered away from the imaging optics as a directly reflected beam 34R because the angle of incidence α must equal the angle of reflection. Scattered light appears as quasi-directional scattered beams 34Q and off-axis scattered beams 34O. The small amount of light energy reaching the prior art apparatus is insufficient to provide any meaningful information about the surface topology of the sclera 33.

Figure 2:
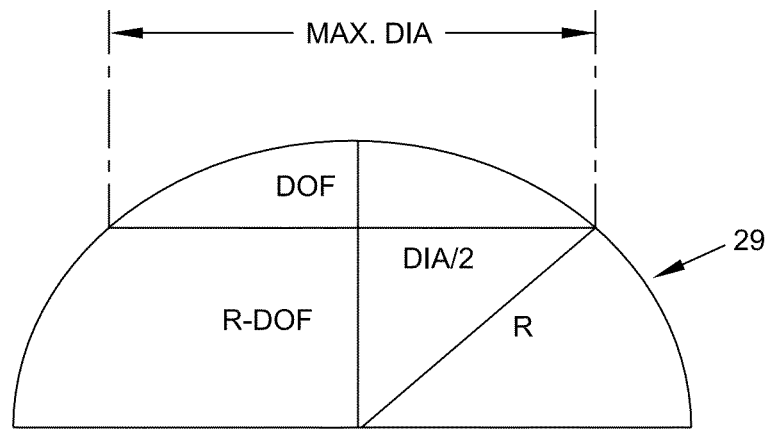
FIG. 2 is a mathematical representation of an eye useful in understanding aspects of this invention.
Figure 3:
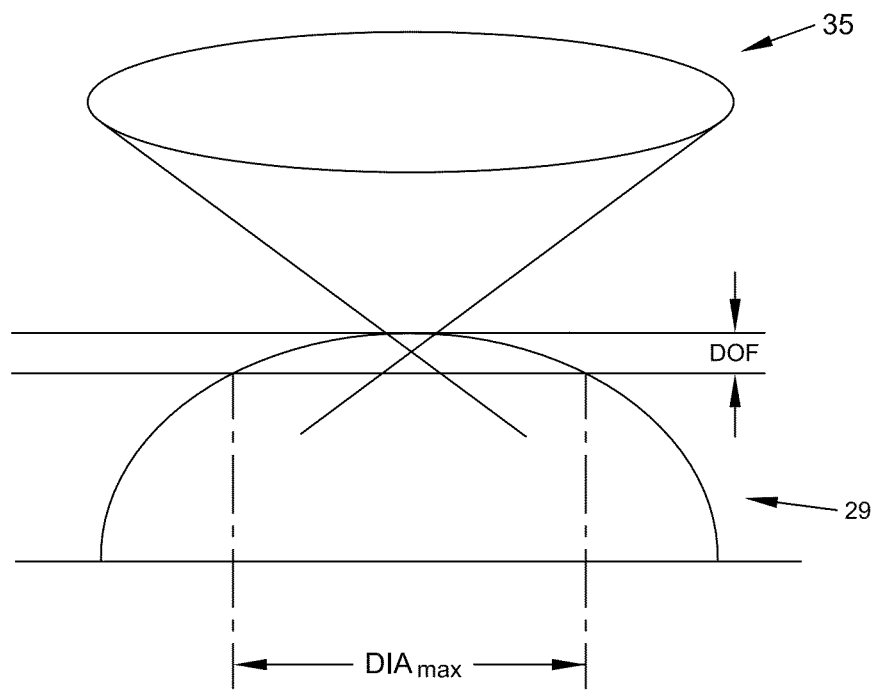
FIG. 3 is a representation of an eye and imaging optics useful in understanding certain aspects of this invention.

A second limitation is the reduction of the signal-to-noise ratio (i.e., image quality) and the lateral resolution of an image which occurs when the optical depth of field is increased to image objects with greater height or depth. FIGS. 2 and 3 illustrate the graphical relationship between the optical depth of field (DOF) and the diameter (DIA) of a region of the eye 29 imaged by OCT apparatus. Equations (1) and (2) describe mathematically to what extent the depth of field (DOF) must be increased to accommodate a larger image diameter.

$$DIA = 2 * \sqrt{R^2 - (R - DOF)^2} \quad (1)$$

and $$DOF = R - \sqrt{R^2 - \left(\frac{DIA}{2}\right)^2} \quad (2)$$

wherein DIA=the maximum measurable diameter, DOF=the depth of field, and
R=the approximate radius of the eye ball.

As known, however, increasing the depth of field (DOF) requires a decrease in the numerical aperture (NA) of the imaging optics and, as also known, $NA^2$ is a measure of the amount of light or signal collect by the imaging optics.

FIG. 3 depicts an imaging lens 35 for imaging the eyeball 29 which exhibits a depth of field (DOF) and maximum measurable diameter ($DIA_{max}$) that can be measured for that depth of field. As also known, NA is given by:

$$NA = \sqrt{\frac{\lambda}{2 * DOF}} \quad (3)$$

wherein λ=illumination wavelength, and NA=imaging optics numerical aperture. As will be apparent, this relationship has adverse effects. First, decreasing NA reduces the lateral resolution by increasing the size of the minimum detectable feature (RES) given by:

$$RES = \frac{\lambda}{2 * NA} \quad (4)$$

Decreasing NA also reduces light collection efficiency and the light collection cone angle of the optics given by:

$$\text{Light Collection Efficiency} \approx NA^2 \quad (5)$$

and $$\text{Light Collection Cone Angle } \theta = 2 * \sin^{-1}(NA) \quad (6)$$

Figure 4:
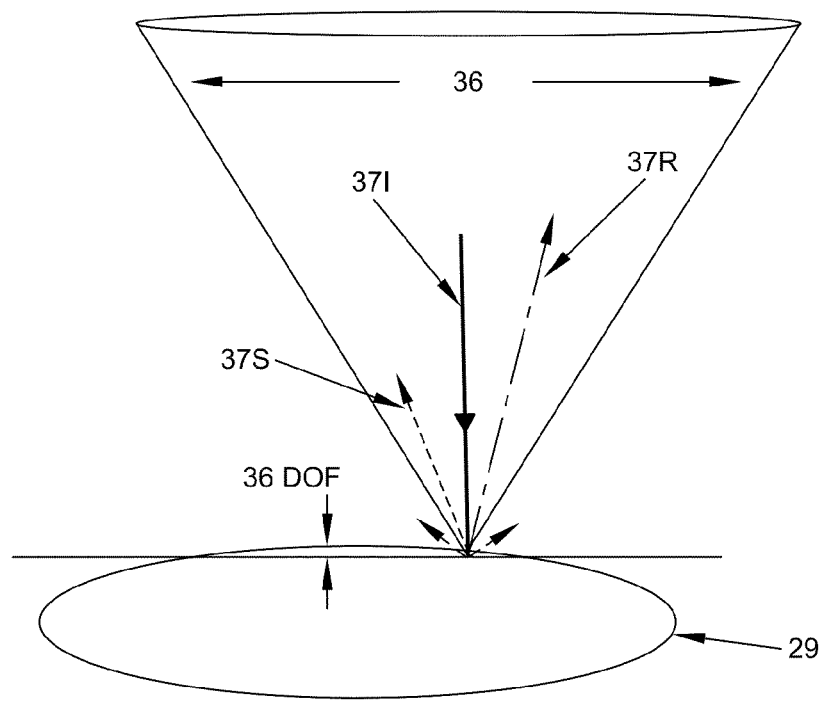
FIG. 4 is another representation of an eye and imaging optics useful in understanding other aspects of this invention.
Figure 5:
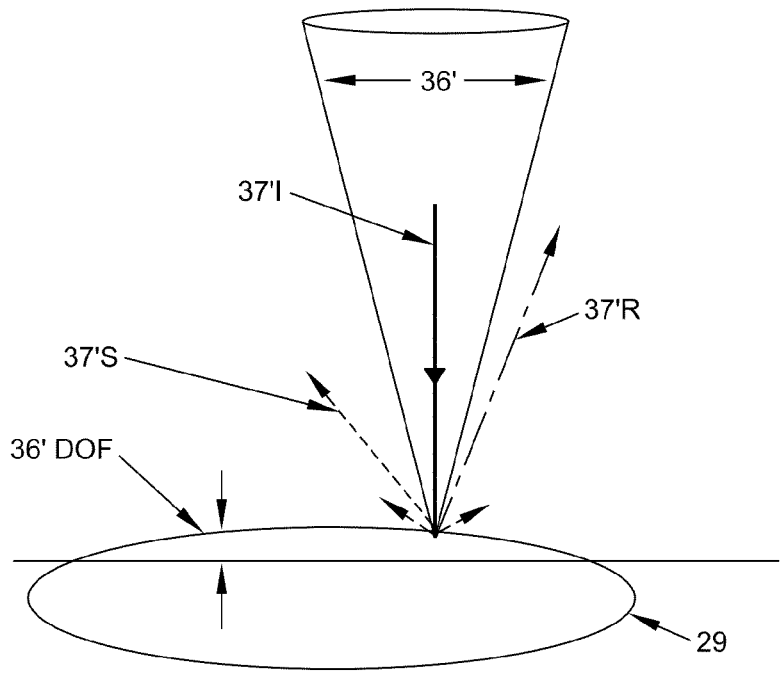
FIG. 5 is still another representation of an eye and imaging optics useful in understanding still other aspects of this invention.

To better understand the effects of reducing the light collection cone angle, consider imaging optics with a cone angle 36 in FIG. 4 and smaller cone angle 36' in FIG. 5. Incident beams 37I and 37'I of light impinging upon the curved surface of an eye 29 reflect along beams 37R and 37'R, and scatter along beams 37S and 37'S, in some combination. When the reflected and scattered light falls within the collection cone angle 36 of the imaging optics, as shown in FIG. 4, this light is captured by the imaging apparatus. With a smaller cone angle 36' in FIG. 5, light falls outside the collection cone angle and is not captured by the optics and cannot provide any information regarding surface topology.

FIGS. 4 and 5 also depict the relationship between cone angle and depth of field wherein a depth of field 36 DOF in FIG. 4 is less than the depth of field 36' DOF in the system with the smaller cone angle 36'.

Table 1 (below) lists the light collection cone angle, depth of focus (DOF), maximum prior art image diameter, resolving power, and light collection efficiency, as a function of the numerical aperture of the prior art imaging optics.

TABLE 1

| | Optical Parameters (Eyeball diameter of 24.5 mm) | | | | |
|---|---|---|---|---|---|
| Numerical Aperture (NA) | Light Collection Cone Angle (degrees) $\theta = 2 \times \sin^{-1}$ (NA) | Depth of Focus $\frac{\lambda}{2 * NA^2}$ $\lambda = 0.55 \mu$ (mm) | Maximum OCT Image Diameter (mm) | Resolving Power for $\frac{\lambda}{2 * NA}$ $\lambda = 0.55$ (microns) | Light Collection Efficiency ($NA^2$) |
| 0.08 | 9.17 | 0.04 | 2 | 3 | $6875 \times 10^{-6}$ — (275x) |
| 0.04 | 4.58 | 0.16 | 4 | 6 | $1718 \times 10^{-6}$ — (68x) |

TABLE 1-continued

Optical Parameters
(Eyeball diameter of 24.5 mm)

| Numerical Aperture (NA) | Light Collection Cone Angle (degrees) $\theta = 2 \times \sin^{-1}$(NA) | Depth of Focus $\dfrac{\lambda}{2 \ast NA^2}$ $\lambda = 0.55 \mu$ (mm) | Maximum OCT Image Diameter (mm) | Resolving Power for $\dfrac{\lambda}{2 \ast NA}$ $\lambda = 0.55$ (microns) | Light Collection Efficiency (NA$^2$) |
|---|---|---|---|---|---|
| 0.03  | 3.43 | 0.37 | 6  | 9  | 743 × 10$^{-6}$—(29x)    |
| 0.02  | 2.29 | 0.67 | 8  | 13 | 410 × 10$^{-6}$—(16.4x)  |
| 0.016 | 1.83 | 1.06 | 10 | 17 | 259 × 10$^{-6}$—(10.36x) |
| 0.012 | 1.37 | 1.57 | 12 | 20 | 144 × 10$^{-6}$—(5.76x)  |
| 0.01  | 1.14 | 2.5  | 14 | 25 | 100 × 10$^{-6}$—(4x)     |
| 0.009 | 1.03 | 3.0  | 16 | 27 | 81 × 10$^{-6}$—(3.24x)   |
| 0.008 | 0.91 | 3.9  | 18 | 31 | 64 × 10$^{-6}$—(2.56x)   |
| 0.007 | 0.80 | 5.17 | 20 | 37 | 49 × 10$^{-6}$—(1.96x)   |
| 0.006 | 0.68 | 6.86 | 22 | 41 | 36 × 10$^{-6}$—(1.44x)   |
| 0.005 | 0.57 | 9.75 | 24 | 50 | 25 × 10$^{-6}$—(1x)      |

Table 1 further illustrates how problematic it can be to image a curved surface. For example, a lens with a numerical aperture of 0.08 has a light collection cone angle of 9.17 degrees but only has a depth of field (DOF) of 0.04 millimeters (40 microns). Therefore the curved surface rapidly goes out of focus as the eye is scanned. This small depth of field can be increased to 9.75 millimeters by using a lens with a numerical aperture (NA) of 0.005, but this reduces the collection cone angle to a miniscule 0.57 degrees. Therefore as the curvature of the eye begins to increase, the reflected and scattered light beams quickly fall outside the cone angle of the imaging optics. Moreover, the total combined reflected and scattered light collected by the imaging optics of a system is proportional to NA$^2$. Therefore, reducing the NA from 0.04 to 0.005, for example, reduces the amount of collected light by a factor of 275. Consequently measurements for determining the surface topology of an individual's eye with prior art systems are difficult, if not impractical.

Figure 6:
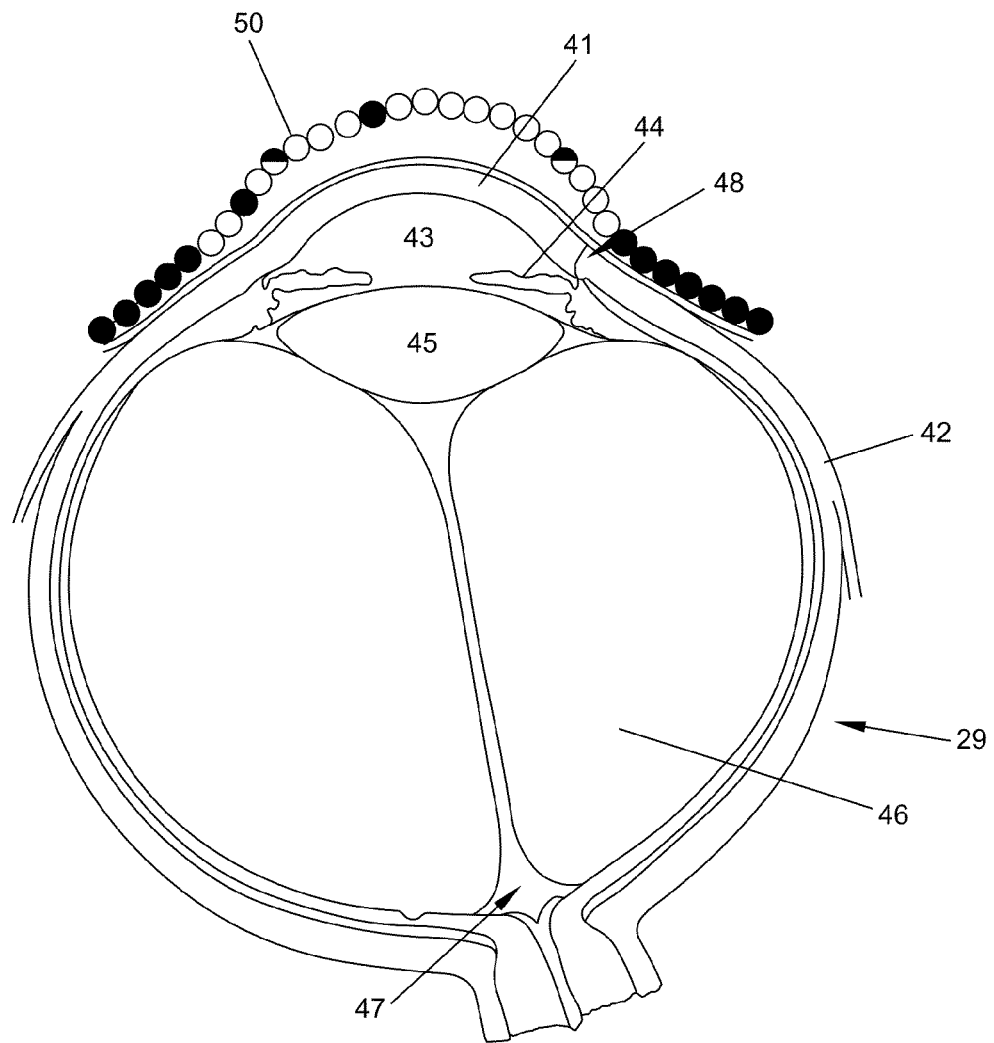
FIG. 6 is a cross section of an eye and with a representation of a scleral lens that is useful in understanding aspects of this invention.
Figure 7:
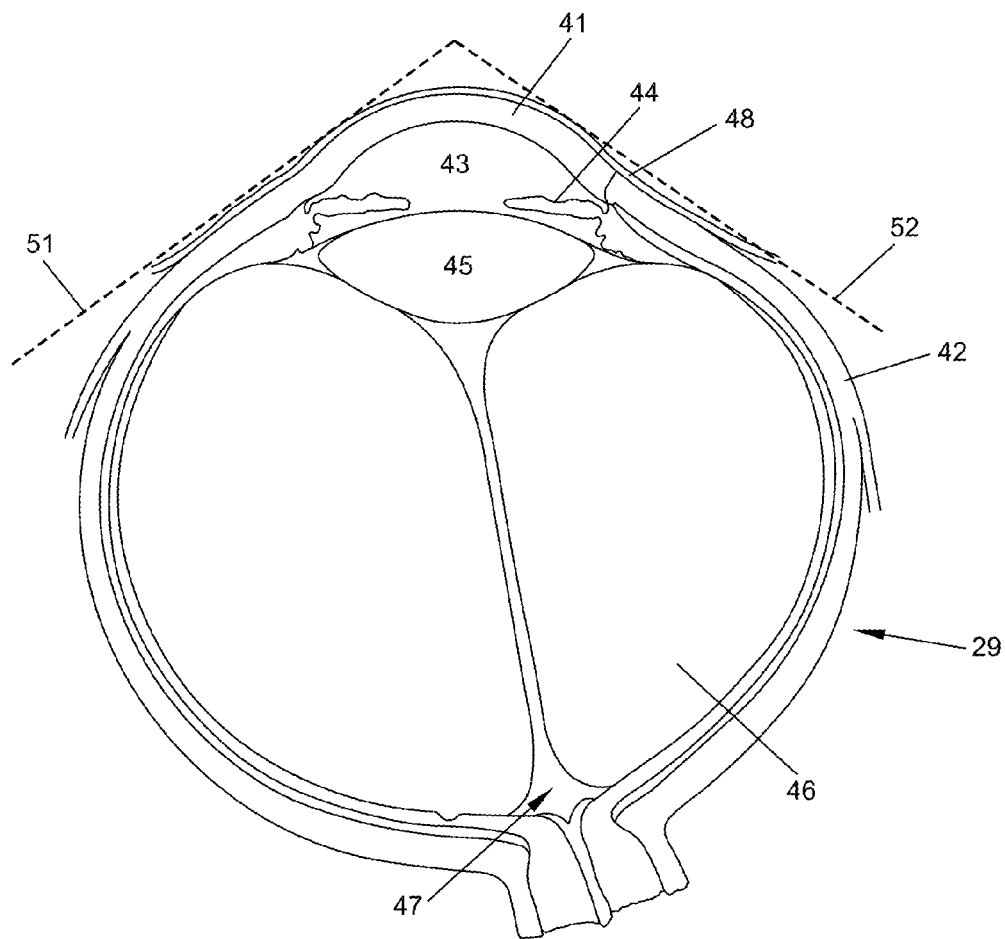
FIG. 7 is a cross section of the eye of FIG. 6 with annotations that are useful in understanding this invention.

With this as background, FIGS. 6 and 7 are illustrations of a human eye 29 with its cornea 41, sclera 42, anterior chamber 43, iris 44, lens 45, vitreous body 46, retina 47 and limbus 48 at the boundary of the cornea 41 and the sclera 42. FIG. 6 depicts a lens 50 that rests on the sclera 42. The requirements for a system to measure the topography of both the corneal and scleral regions of the eye in FIGS. 6 and 7 should include a maximum profile diameter of 24 mm with a depth of field of 12 mm. Moreover the system must be sufficiently fast to prevent eye motion from adversely impacting the acquisition of the data during a scan.

As shown in FIG. 1, when the eye 29 is illuminated by an apparatus from an angle perpendicular to the surface of the cornea 41 (i.e., vertically in FIG. 1) the light angle of incidence and reflectance rapidly increases as one laterally scans across the sclera 42 toward the outer extremities of the eye. If, however, one views the eye from an angle and off to the side relative to the top of the corneal surface, the outer regions of the cornea 41 and sclera 42 can be shown to lay along dashed tangent lines 51 and 52 as indicated in FIG. 7.

Figure 8:
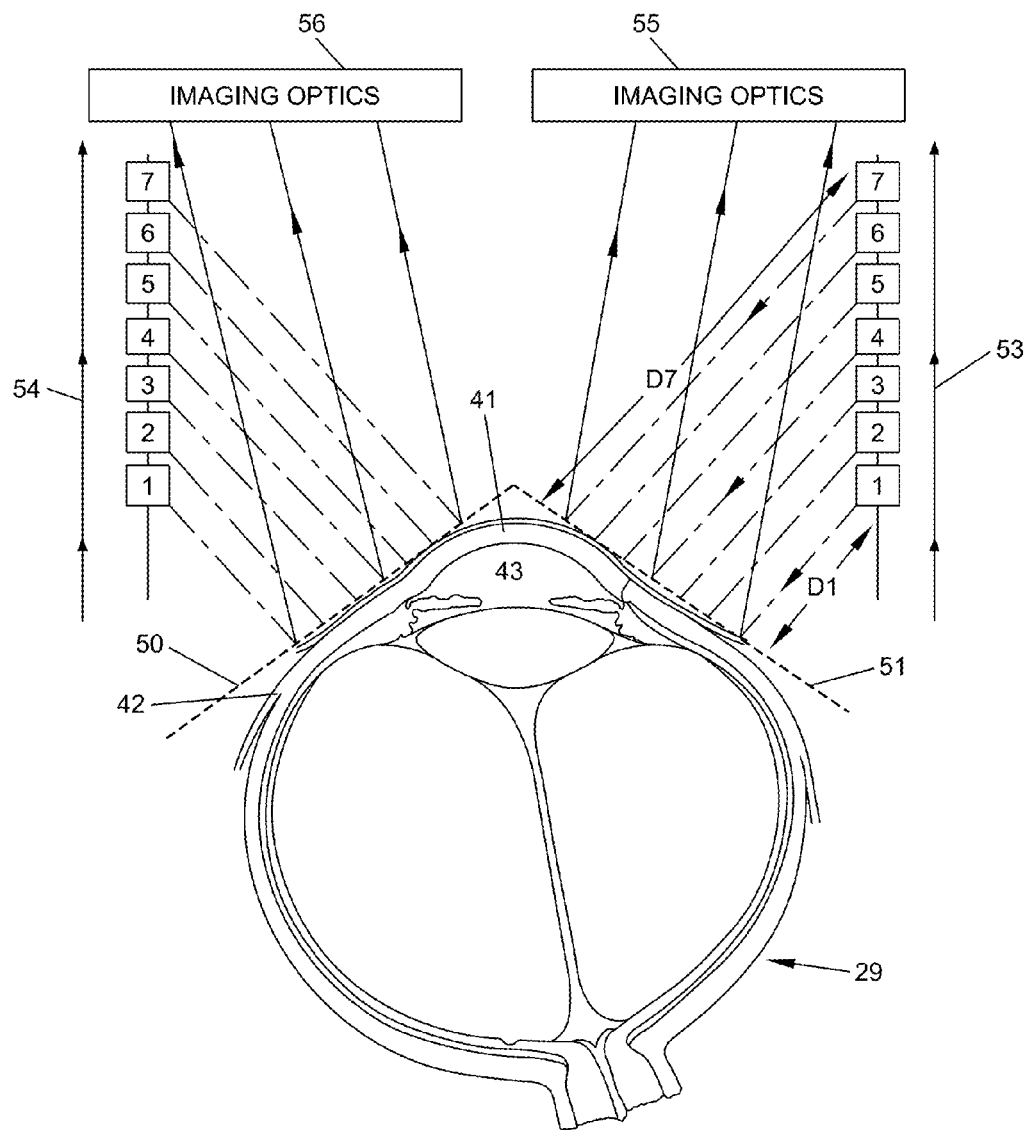
FIG. 8 is a cross section of the eye of FIG. 6 with a functional view of a first embodiment of apparatus incorporating this invention.

Now referring to FIG. 8, one method for measuring the curvature of the sclera 42 and the cornea 41 involves establishing a "tangent" line 50 or 51 at the surface of the eye overlying portions of the cornea and adjacent sclera and placing a source 53 or a source 54 for an optical beam onto a linear track with the beam oriented at a given angle (θ) relative to the dashed tangential lines 51 and 50 respectively. It has been found that an angle of 27°<β<47° relative to an axis perpendicular to the top of the pupil provides improved results. A value of about 37° has been used successfully. Functionally, as each of the sources 53 and 54 moves away from the eye along a track through positions 1 to 7, the corresponding incident beam laterally traverses across the surface of the eye moving from the outer extremes of the sclera 42 toward and onto the cornea 41. Throughout the entire duration of the scan the angles of the incident beam, reflected and scattered beams remain approximately the same, varying only slightly due to small perturbations in the surface of the eye.

Figure 9:
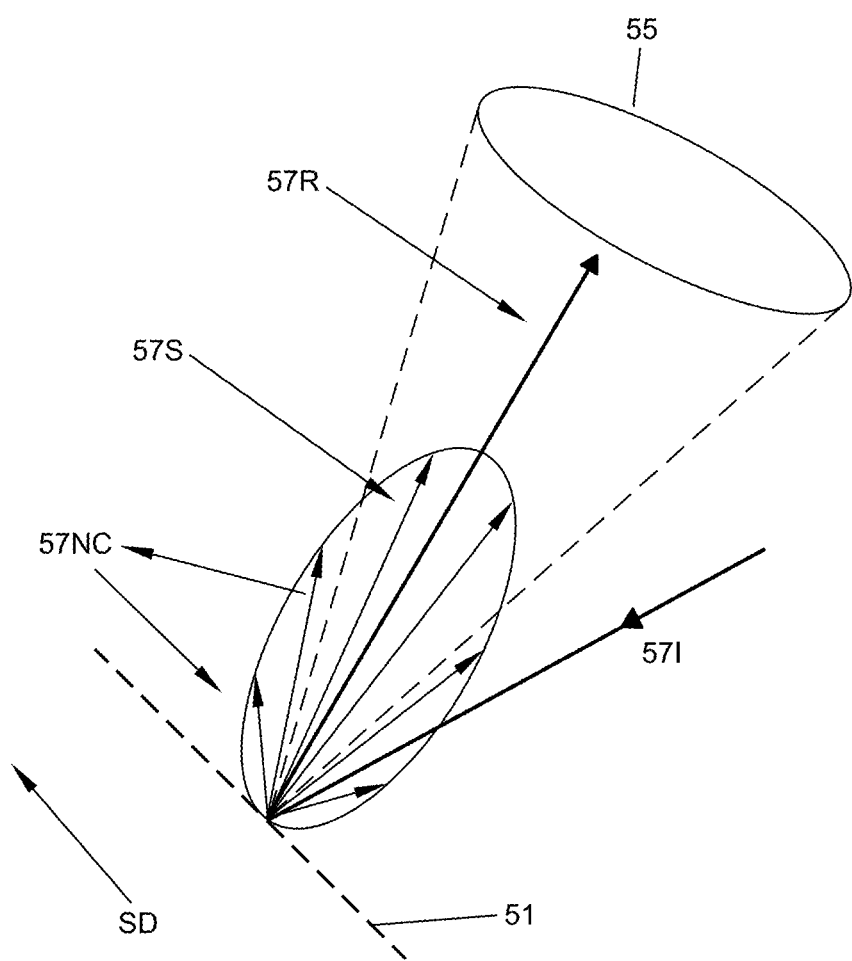
FIG. 9 is a functional view of imaging optics useful in understanding this invention.

Referring to FIG. 9, when an incident beam 57I impinges upon the surface of the eye at a position along a tangent line, such as tangent line 51 and the eye 29 is scanned in a direction represented by an arrow SD, the light beams returning from the surface are composed of a directly reflected component 57R and multiple scattered components 57S which in total form an oval shaped spatial distribution of optical energy referred to as the surface's Bidirectional Reflectance Function. In a specific embodiment of this invention the angles of the incident beam and imaging optics are optimized to collect the strongest signal for scanning of the sclera and corneal regions.

Figure 11:
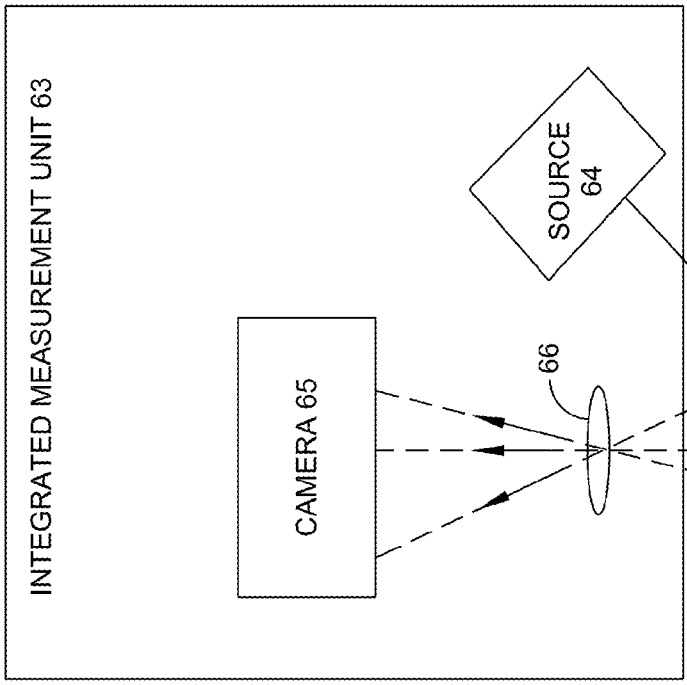
FIG. 11 is a block diagram of another implementation of a profile measurement unit.
Figure 10:
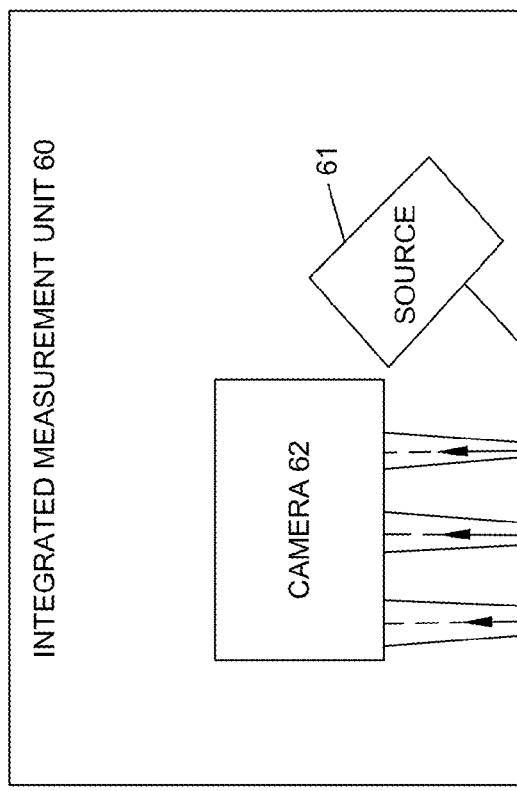
FIG. 10 is a simplified block diagram of one implementation of eye scanning apparatus that is used as a profile measurement unit and that includes features of this invention.

FIGS. 10 and 11 show the use of telecentric and non-telecentric optics, respectively, to collect the directly reflected and quasi-directional scattered light beams from an eye and to provide a distance measurement using triangulation. FIG. 10 depicts an integrated measurement unit 60 which packages an incident light beam source 61 and a camera with telecentric imaging optics. FIG. 11 depicts another embodiment comprising an integrated measurement unit 63 with an incident light beam source 64 and a camera 65 with non-telecentric imaging optics 66.

It is important that the data acquired from all radial measurements be spatially aligned to each other and to the same known spatial position in the eye. Therefore, as is true in many measurements of the eye, the eye should not move during the data acquisition process. It has also been reported that torsional saccades of 5 or 10 degrees may occasionally occur even during steady fixation.

When measuring the profile, it is useful to know the approximate location of the limbus 48 shown in FIG. 7 to calculate the optimal location at which the contact lens should lift or begin to raise above the sclera 42. However, obtaining an accurate smooth topology map is very difficult because the optical light reflection and scattering properties (Bidirectional Redistribution Functions) of the sclera 42 and cornea 41 are different. The sclera 42 is white with a shiny surface which produces a relatively strong reflected and directionally scattered signal. In comparison, the cornea 41 is clear and designed by nature to transmit, not reflect, light; therefore both the directly reflected and directionally scattered optical components from the cornea 41 are relatively weak.

Camera signal output when viewing different regions of the eye is given by the equation:

$$Cam_{sig} \approx [(ILLUMIN*REF*TIME_{INTEGRATION}*NA^2*K) + NOISE]*Eg] \quad (7)$$

wherein:
ILLUMIN=total illumination power incident on the eye
REF=the percent of illuminated light either reflected or scattered off the surface of the eye being scanned and is given by:

$$REF = \frac{(REFLECTED + SCATTERED)LIGHT\ INTENSITY}{ILLUMINATION\ ON\ LIGHT\ INTENSITY} \quad (8)$$

$TIME_{INTEGRATION}$=time duration over which light is collected by the camera
$NA^2$=the (numerical aperture) of the imaging optics and is a measure of how much of the reflected and scattered light is collected by the imaging optics
K=optical power to electronic signal conversion constant for the camera,
NOISE=electronically introduced noise of the camera electronics when viewing a dark field, and
Eg=electronic gain or amplification of the camera signal.

Equation (8) can be expressed in terms of optical gain (Og) and electronic gain Eg, such that:

$$Cam_{sig} \approx [(REF*Og) + NOISE]*Eg \quad (9)$$

where $$Og = [ILLUMIN*REF*TIME_{INTEGRATION}*K)] \quad (10)$$

Qualitatively, from equation (9):
[Og×Ref]>NOISE in order to detect signals from the scanned region of the eye,
Increasing electronic gain, Eg, increases the magnitude of the NOISE in the camera output signal, and
Increasing electronic gain Eg does not improve the signal to noise ratio as:

$$S/N = \frac{Og*REF}{NOISE} \quad (11)$$

When scanning the sclera 42, its smooth white surface returns much of the illumination beam to the camera creating a strong electronic signal so both the optical gain, Og, and electronic gain, Eg, can be kept at minimal levels. This implies the use of minimal illumination power since optical gain OG is proportional to illumination intensity. In comparison, detection of the surface of the cornea 41 requires much greater optical and electronic gain due to the weakly reflected and scattered signal levels from the cornea. Detection of the corneal surface is further complicated because the camera simultaneously receives two signals, a weak signal from the cornea and a much stronger signal from the underlying iris, as shown in FIG. 12.

Figure 12:
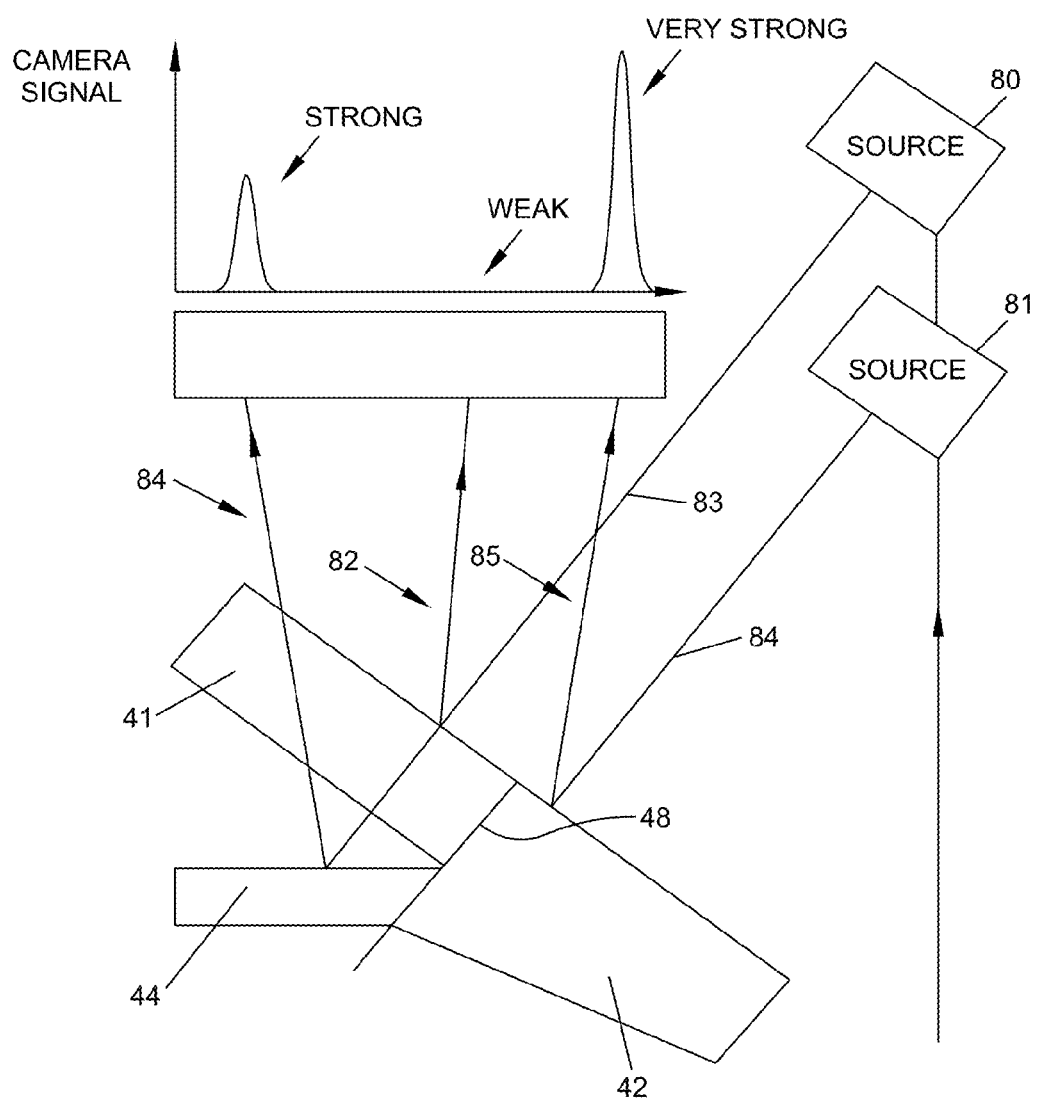
FIG. 12 is a block diagram that is useful in understanding aspects of this invention.

Referring to FIG. 12, when a source is at location 81, its incident beam 84 strikes the sclera 42 and reflects and scatters a strong signal represented by beam 85 back toward the camera. When the illumination beam scans over the cornea 41 with the source at location 80, the source beam impinges upon the surface of the cornea 41 and only a small percentage of the power is reflected and scattered back to the camera as shown by beam 82. The majority of the power transmits through the cornea as shown by illumination beam 83 impinging upon the surface of the iris 44, which in turn reflects and scatters a much stronger signal represented by beam 84 back toward the camera. It will also be observed from FIG. 12, that the spatial locations of the beams imaged onto the camera from the cornea and iris are different. However, since both beams simultaneously strike the camera, a profile measurement unit must control both the electronic gain (Eg) and optical gain (Og) in real time as the eye is scanned spatially and in real time as the signal is read out of the camera for a given spatial position along the cornea.

Figure 13:
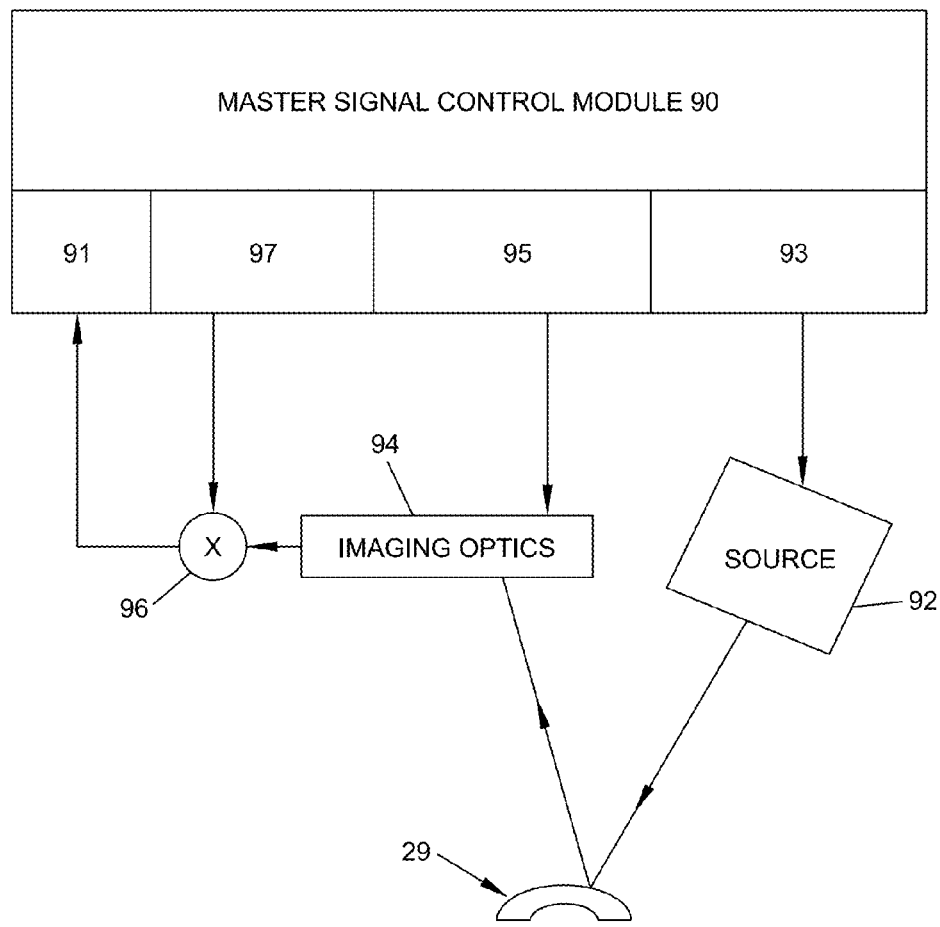
FIG. 13 is a block diagram of a system implementation that incorporates this invention.

In accordance with this invention, in essence each signal peak representing the sclera, cornea, and iris has the electronic gain and optical gain automatically optimized for processing of the signal. Optical gain is adjusted by varying the camera integration time ($TIME_{INTEGRATION}$), illumination power (ILLUMIN) and illumination pulse width (PW). A Master Signal Control Module 90 shown in FIG. 13 provides such optimization. The Master Signal Control Module 90 includes a camera signal analyzing module 91 which has the capability of controlling illumination power and pulse width from a source 92 through an illumination control module 93. The analyzer module 91 also adjusts camera or optical sensor integration time through control module 95, and the magnitude of the camera output which is fed to an amplifier 96 under the control of electronic gain control 97.

More specifically, such a master signal control module 90 can be implemented as follows:

A. Predetermined minimum and maximum values are set for the electronic gain, Eg in the module 97, camera integration time ($TIME_{INTEGRATION}$) in the module 95, illumination intensity (ILLUMIN) and illumination pulse width (PW) in the module 93 such that:

$$Eg_{min} \leq Eg \leq Eg_{max}$$

$$TIME_{INTEGRATIONmin} \leq TIME_{INTEGRATION} \leq TIME_{INTEGRATIONmax}$$

$$IL_{min} \leq ILLUMIN \leq IL_{max}$$

$$PW_{min} \leq PW \leq PW_{max}$$

B. Referring to FIGS. 12 and 13, when the sclera 42 is scanned, a strong signal is received. When this occurs, the modules 97, 95 and 93 set Eg, $TIME_{INTEGRATION}$ and Pw to minimal values via the feedback loop provided by the analyzer 91 that monitors the camera or optical sensor signal level.

C. When the scan reaches the Limbus 48, the weakly returned signal from the cornea 41 immediately causes electronic gain Eg and Optical Gain (Og) to be increased.

D. When a scan reaches the iris 44, the stronger signal from the iris 44 is examined, temporally later in the same camera output line, and the optical and electronic gains are reduced.

As previously stated, optical gain is a function of: integration time, illumination pulse width and illumination power variables. The order in which these variables are increased and decreased is programmable. The readout time of the camera or optical sensor and processing time of the Master Signal Control Module 90 FIG. 13 must be very fast relative to the spatial scan rate of the profile measurement units to insure that multiple measurements of repetitive data can be read out of the camera and the various parameters adjusted while the camera or optical sensor is still looking at the same position on the eye.

Figure 14:
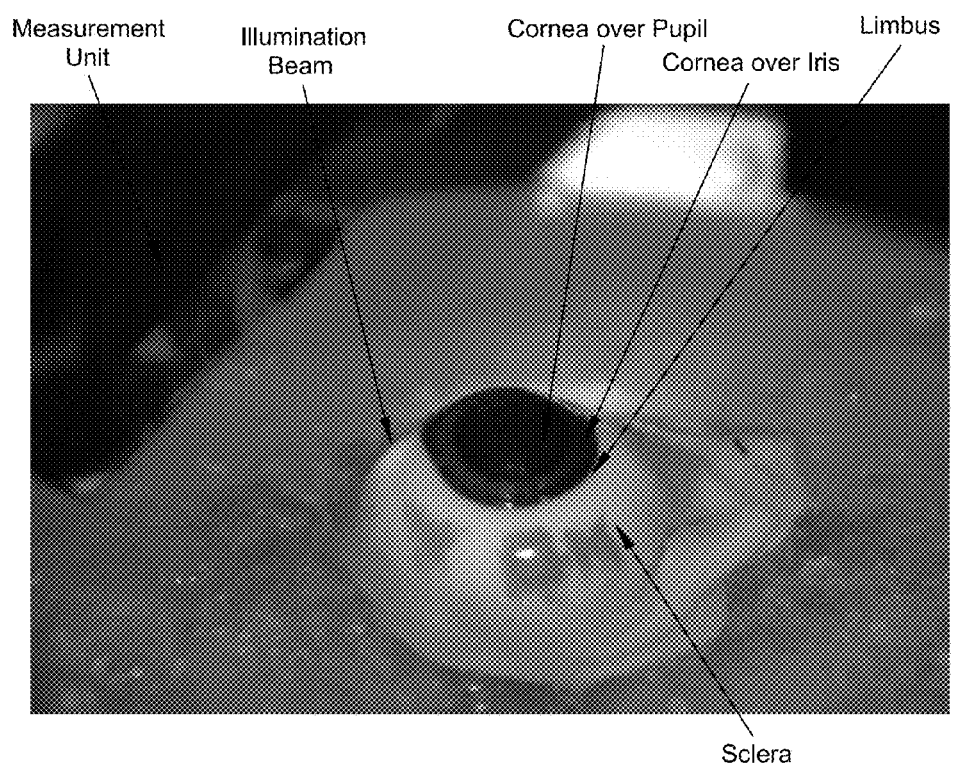
FIG. 14 is an image of an animal eye annotated to disclose regions of interest.
Figure 15:
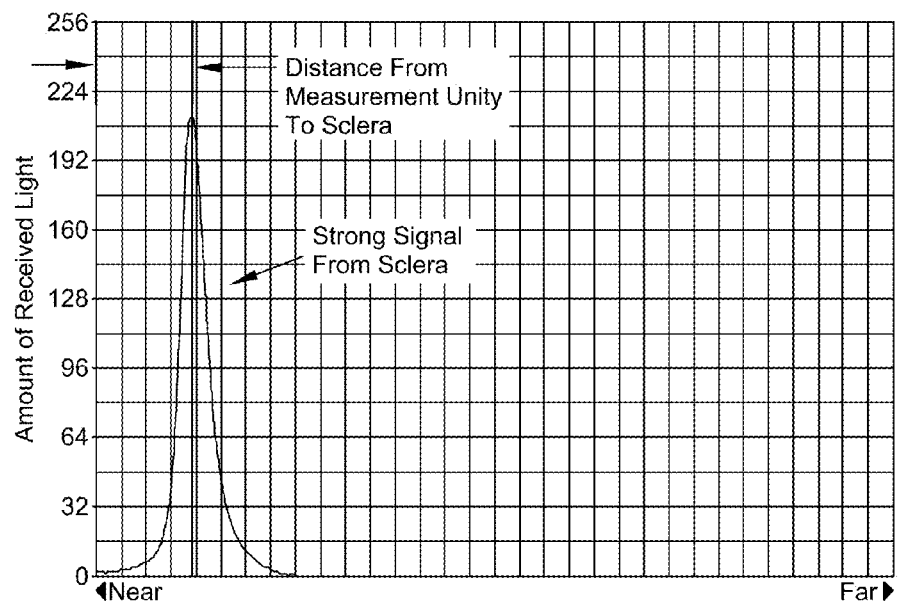
FIG. 15 is a graph of the signal from the scleral region generated by apparatus incorporating this invention during a scan of the eye in FIG. 14.
Figure 16:
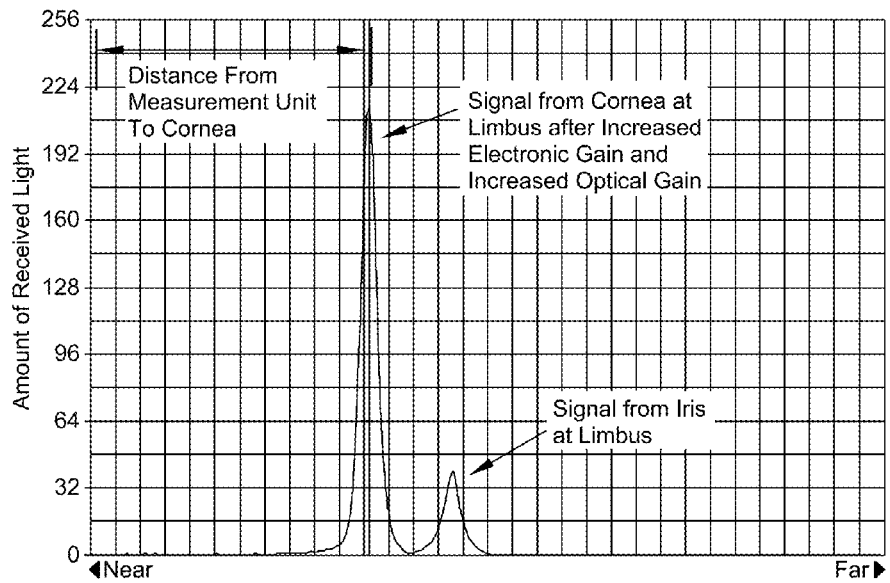
FIG. 16 is a graph of the signal from the limbus region generated by apparatus incorporating this invention during a scan of the eye in FIG. 14.
Figure 17:
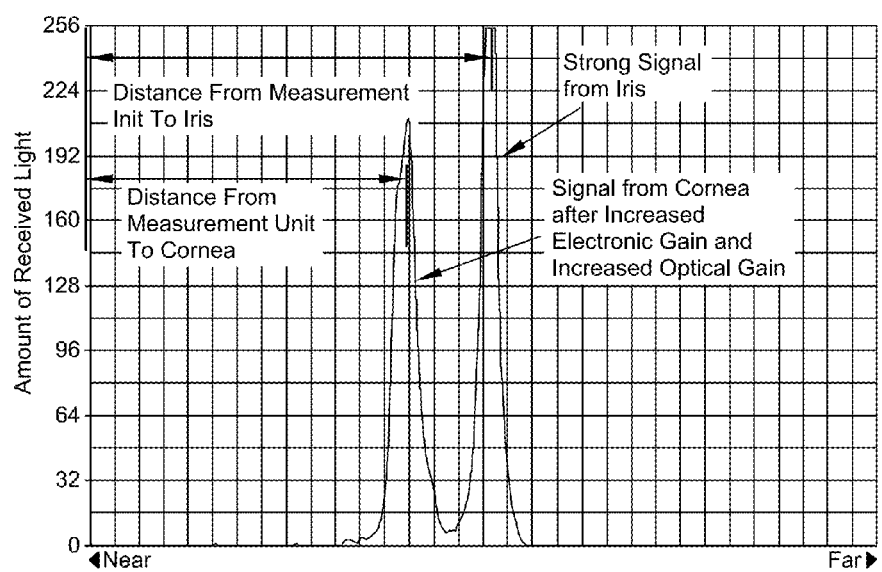
FIG. 17 is a graph of the signal from the corneal region generated by apparatus incorporating this invention during a scan of the eye in FIG. 14.
Figure 18:
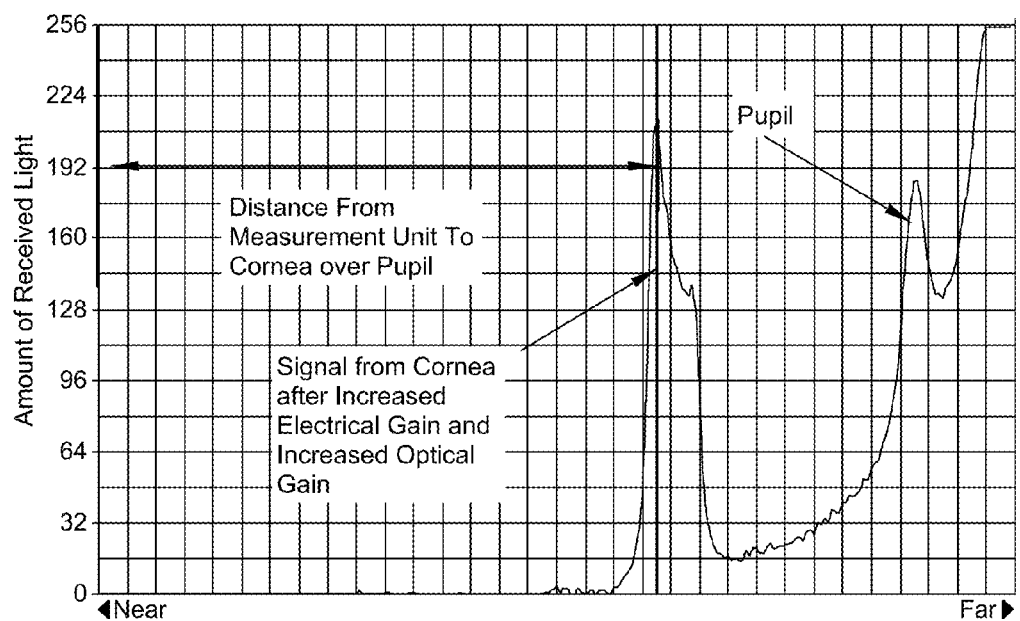
FIG. 18 is a graph of the signal from the corneal and pupil regions generated by apparatus incorporating this invention during a scan of the eye in FIG. 14.

Each Profile Measurement Unit can be implemented using individual components or by using a laser displacement sensor. Such sensors incorporate a laser illumination source, a high speed CMOS camera sensor, and electronics to adjust the illumination power, illumination pulse width, sensor integration time, and sensor gain in real time and to provide distance at successive locations along a scan line. Such a sensor was incorporated into a Profile Measurement Unit configured in accordance with the optical, mechanical, electronic, and processing parameters described above to enable detection of the sclera, Limbus, and corneal regions of a pig eye as shown in FIG. 14. The pig eye was placed in a dish and scanned with one Profile Measurement Unit. FIG. 15 shows the detection of the sclera and its distance from the known position of the Profile Measurement Unit. FIG. 16 shows the detection of the Limbus, indicating the position of the cornea and the beginning of the iris. FIG. 17 shows signals from both the cornea and iris, and FIG. 18 shows signals from the cornea and pupil. The underlying data from which these graphs were plotted can then be assimilated to create surface contours of the scleral and corneal regions of the eye.

It has been found that a source beam of shorter wavelength, such as blue light, will produce a greater percentage of light that is reflected and scattered toward the optical sensor than for a source beam of a longer wavelength such as red light. Experiments have demonstrated that red light reflected from the cornea is 208/(256+208)×100%=45% and the light reflected from the iris=256/(256+208)×100%=55% indicating that more light is reflected from the iris than from the surface of the cornea. If the cornea were to become very thin, as with Keratoconis patients, the two reflected red beams will spatially move together on the surface of the optical sensor making it difficult to accurately detect the spatial position of the thin cornea. When the cornea is illuminated with the shorter wavelength blue light the cornea reflects 180/(72+180)×=72% of the light and the iris reflects 28%. The signal from the cornea is 2.5 times stronger than the signal from the iris to facilitate detection of the corneal surface.

Referring again to FIGS. 8, 10 and 11, this system includes an imaging unit and optical source. In FIG. 8 the optical source moves along a path 53 while directing illumination from the source to the eye 29 essentially normal to the tangent line 51. In FIGS. 10 and 11 the integrated source/optical sensor moves along path 53 while directing illumination from the source to the eye 29 essentially normal to the tangent line 51. During each scan, it is necessary to move the source in FIG. 8 and integrated source measurement units 60 and 63 in FIGS. 10 and 11. The components of such an integrated measurement 60 or 63 produce a structure with significant weight with attendant mass and inertia problems that arise when moving such structures rapidly over a short distance. This may limit the ability of such apparatus to attain all of the benefits of this invention.

Figure 19:
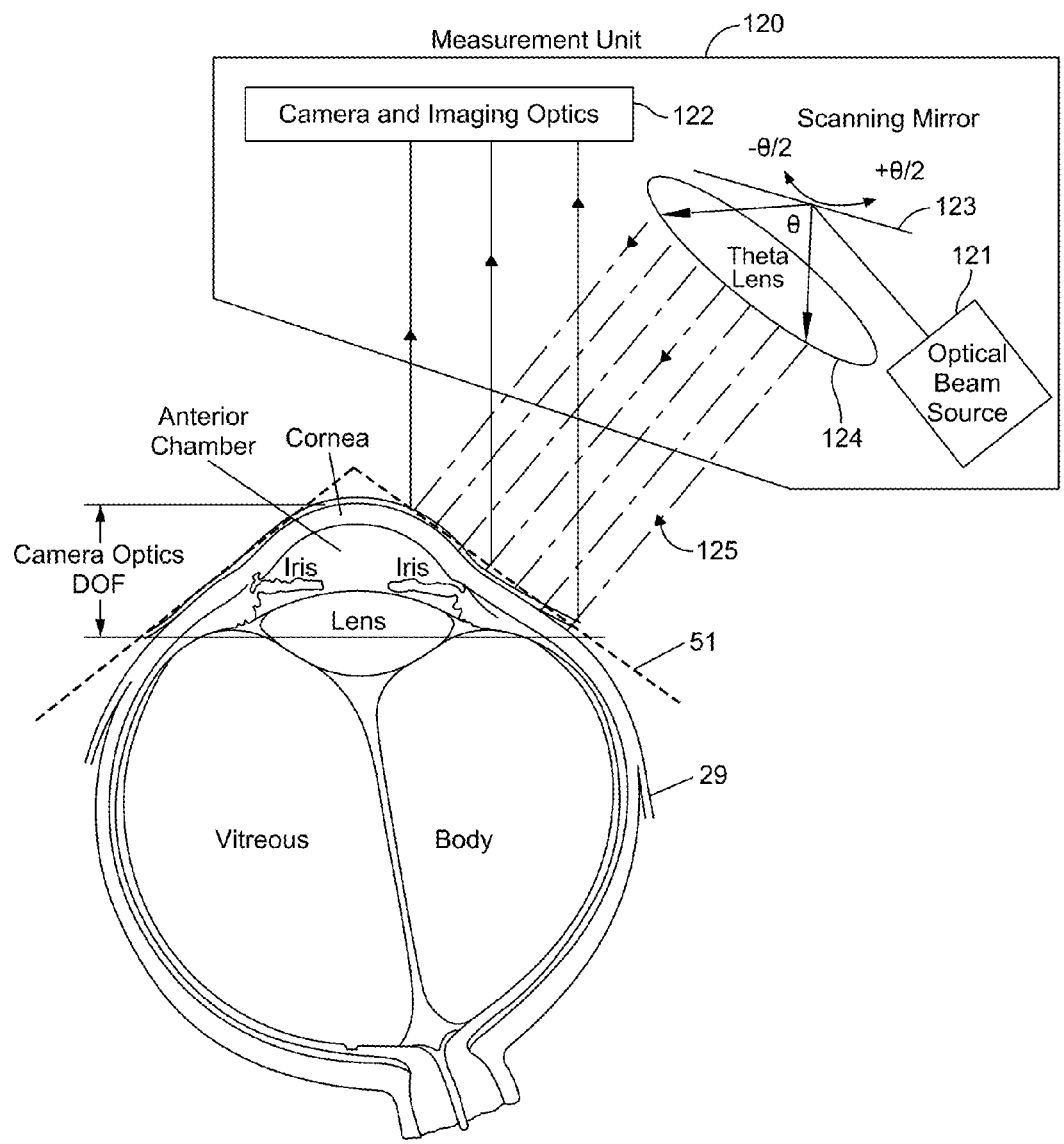
FIG. 19 schematically depicts the organization of a second embodiment of apparatus incorporating this invention.

FIG. 19 depicts an alternative embodiment of a triangulation measurement unit 120 that includes an optical beam source 121 and camera and imaging optics 122. As these components are contained within unit 120, they undergo no motion during a single scanning operation relative to the measurement unit 120. Illumination from the optical beam source 121 is directed to an extremely lightweight scanning mirror 123 contained within measurement unit 120. The scanning mirror undergoes an angular displacement of ±θ/2. Light energy reflecting from the mirror 123 is directed to a theta lens 124. As known in the art, a theta lens redirects light received along different axes from a source such as the scanning mirror 123, along parallel axes as shown by dashed lines 125 between the theta lens 124 and the tangent line 51 at the eye 29. This illumination pattern has the same characteristics as the pattern of FIG. 8, but in this embodiment the only moving element is the scanning mirror 123 that has minimal weight.

Figure 20:
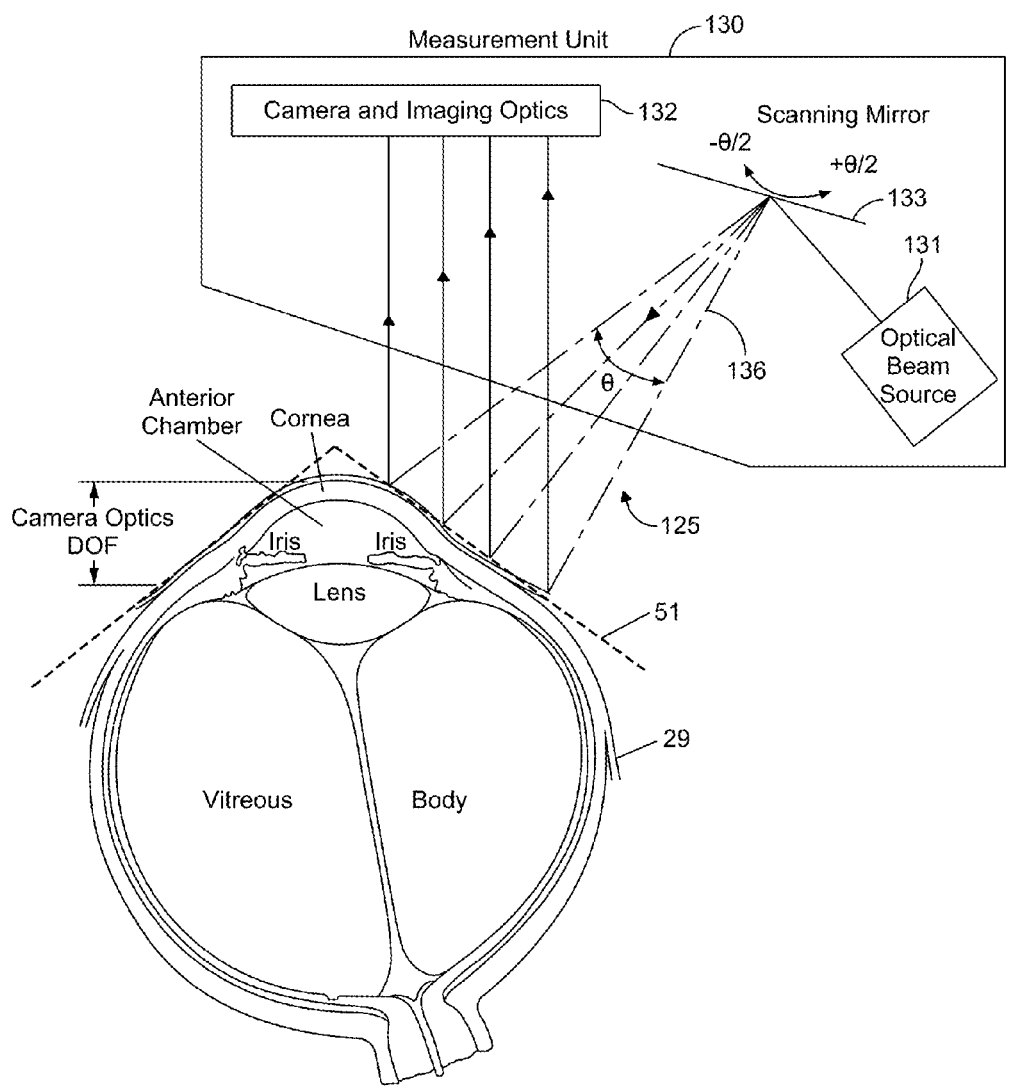
FIG. 20 schematically depicts a third embodiment of apparatus incorporating this invention.

As another alternative triangulation unit, FIG. 20 discloses an integrated measurement unit 130 with a fixed optical beam source 131 and camera and imaging optics 132, but without a theta lens. In this configuration, the light is transmitted from a mirror 133 directly along the lines 136 as they travel from the mirror 133 to the tangent plane 51 as the scanning mirror 133 rotates through its operating angle. At reasonable measurement ranges, it may be possible to scan the cornea and sclera of an eye by moving the scanning mirror through a limited range of motion (e.g., ±5° for a measurement distance of 100 mm away from the eye). As previously indicated, the reflected light from the cornea and sclera acts according to a Bidirectional Reflection Function (FIG. 9). Consequently, over a small angular range of scanning mirror motion the imaging optics should be able to collect a strong signal over the entire scan segment of the eye without significant variation or error. Such a configuration, while not producing an illumination beam as parallel to the tangent as the theta lens system of FIG. 19, minimizes or eliminates the need for the theta lens and its attendant support structures thereby reducing the number of optical components in the unit 130 and the overall weight of the unit 130. Weight of the measurement unit is a consideration when constructing apparatus for revolving the measurement unit 130 about the eye to allow successive scans to be taken and angularly displaced locations.

Figure 21:
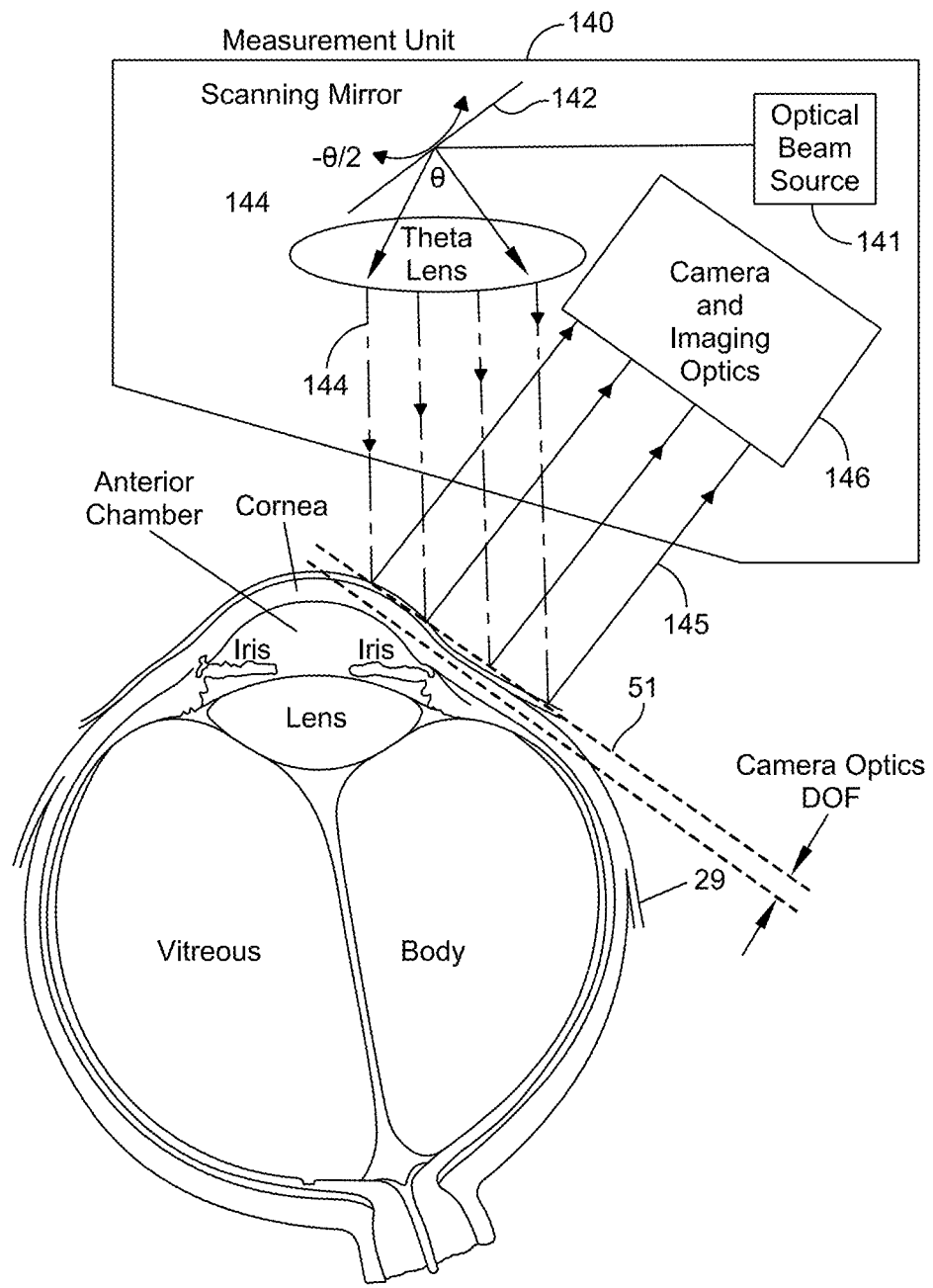
FIG. 21 depicts a fourth embodiment of apparatus incorporating this invention.

FIG. 21 depicts still another measurement unit 140 variation wherein the positions of the scanning mirror and the camera and imaging optics change. The integrated measurement unit 140 includes an optical beam source 141 that directs light to scanning mirror 142 and through a theta lens 143. The theta lens 143, in turn, redirects light along parallel paths 144 to intersect the tangent line 51 at an oblique angle in the range of about 27° to 47° relative to an axis perpendicular to the top of the pupil; in one embodiment the angle is selected to be about 37°. Light reflected from the eye 29 travels nominally along parallel paths 145 to camera and imaging optics 146.

Referring to FIGS. 19 and 21, in FIG. 19 the camera optics depth of field (DOF) must be sufficient to provide focus over all the intersections of the light rays between the outer illuminating rays 125 with the eye surface proximate the tangent line 51. The apparatus FIG. 21 minimizes the depth of field requirements because all the reflective eye surfaces of interest (e.g., portions of the cornea, the sclera and limbus) lie in a narrow range of distances from the camera and imaging optics 146.

Figure 22:
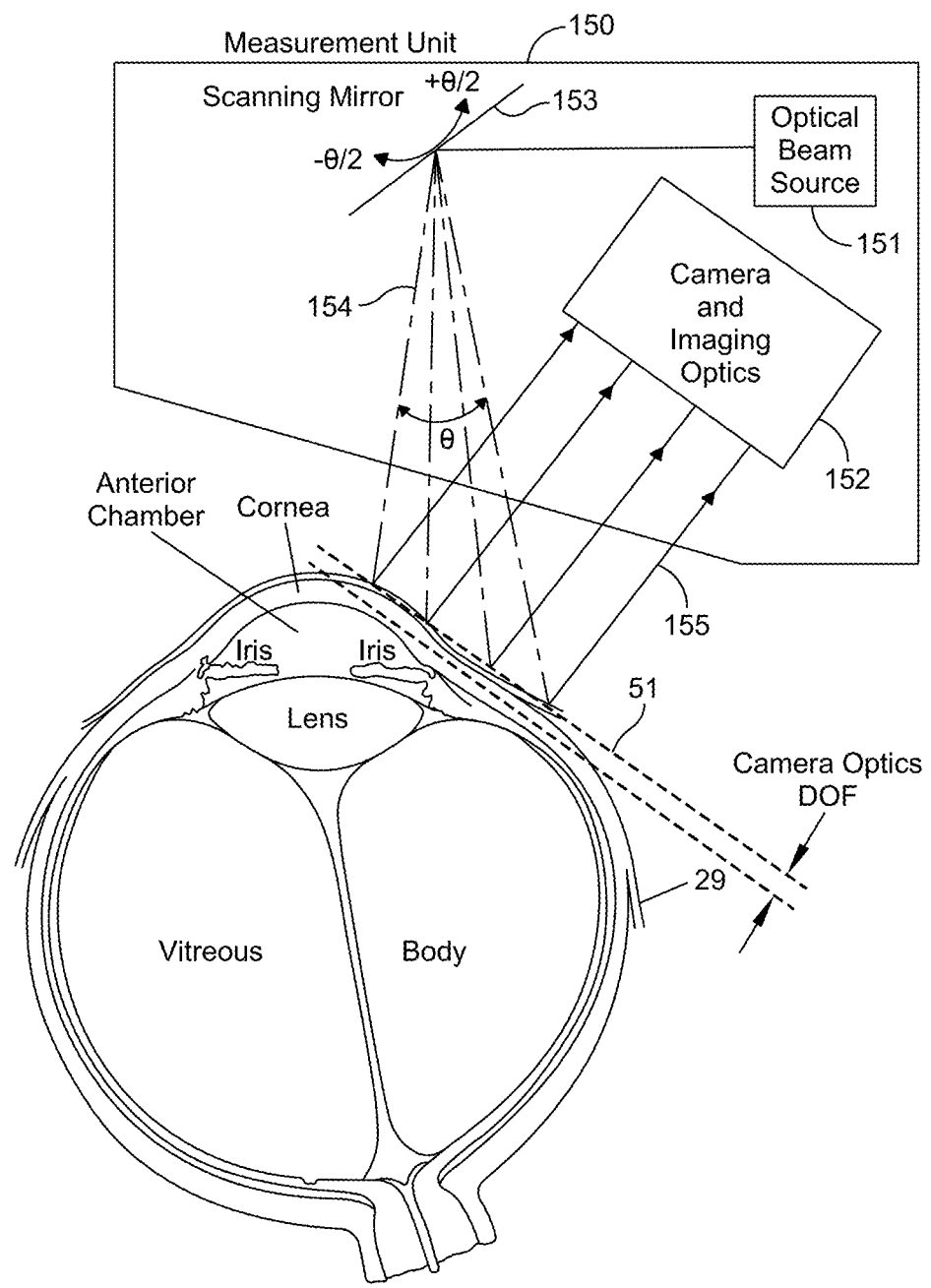
FIG. 22 depicts a fifth embodiment of apparatus incorporating this invention.

The configuration of FIG. 22 provides a similar advantage over the configuration of FIG. 20. In FIG. 22 an integrated measurement unit 150 includes an optical beam source 151 that directs light to a scanning mirror 153 which, in turn, redirects light along the angularly displaced path lines 154 toward the eye surfaces along the tangent line 51. Light reflects and is scattered back from the illuminated portions of the sclera, cornea and limbus to the camera and imaging optics 152 along lines 155 to obtain meaningful data. Again as the camera and imaging optics 152 are oriented to receive light reflected along lines 155 that are normal to the tangent 51, the required depth of field for the optics in FIG. 22 is significantly reduced as compared to the depth of field requirement for FIG. 20.

Figure 23:
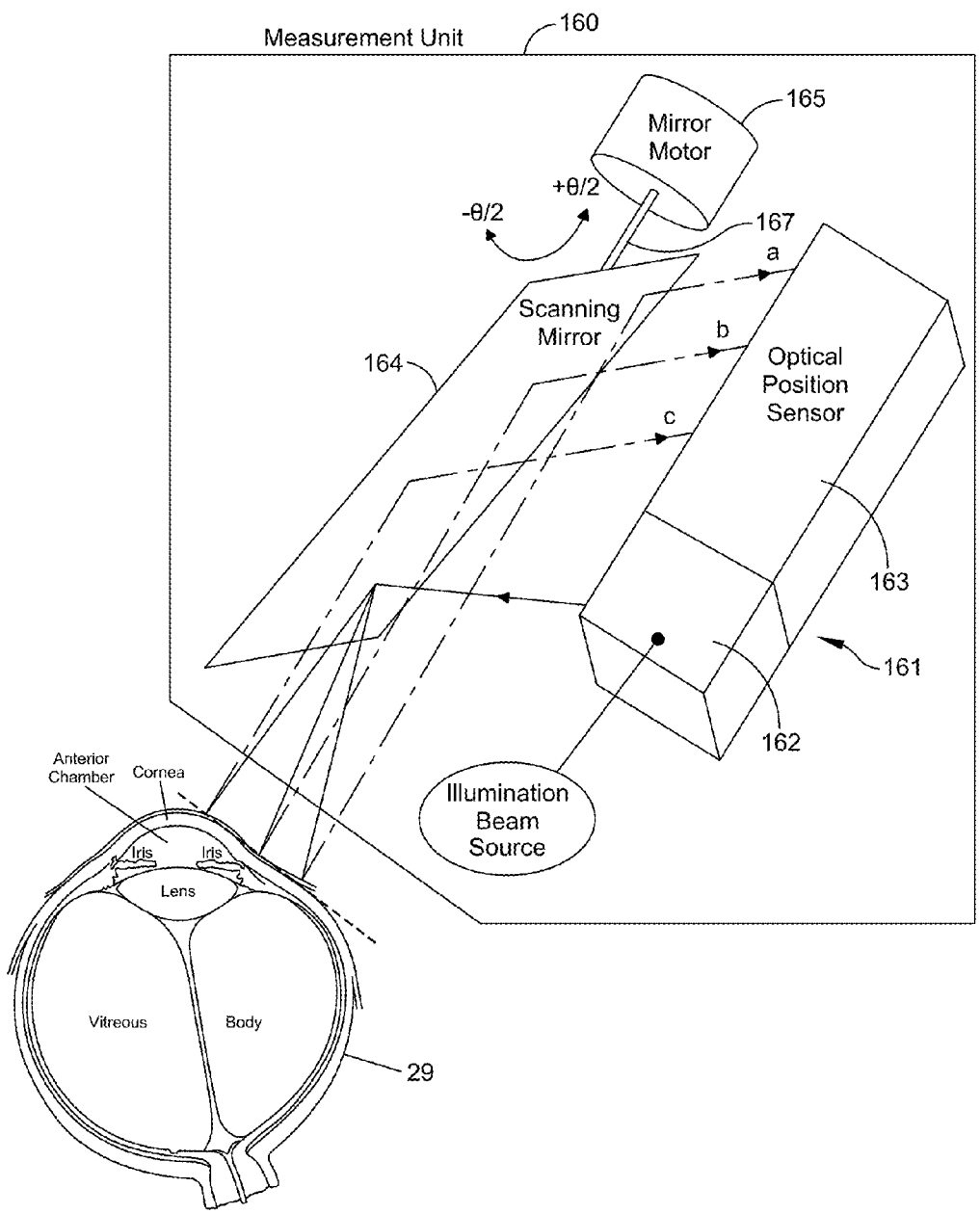
FIG. 23 depicts a sixth embodiment of apparatus incorporating this invention.

FIG. 23 depicts an alternate version of the measurement unit 160 which includes a triangulation sensor 161 with an integrated illumination source 162 and an optical position sensor 163. The illumination source 162 directs a beam to a scanning mirror 164 that a motor drive 165 oscillates about a narrow angular range (e.g., ±θ°). As the illumination beam from the illumination source 162 is scanned across eye 29, it is reflected and scattered toward the scanning mirror and back to the optical position sensor. It is displaced on the position sensor, such as at points "a", "b" and "c" as scanning mirror 164 oscillates on a shaft 167 and corresponding axis. In FIG. 23 the long axis of the scanning mirror and the long axis of the integrated source beam—optical sensor triangulation unit are perpendicular to the plane of the page. As the source beam scans the meridian along the tangent line, drawn in the plane of the page, the orientation of the optical position sensor within the triangulation unit and hence light rays corresponding to beams "a", "b" and "c" are perpendicular to the direction of the page.

Figure 24:
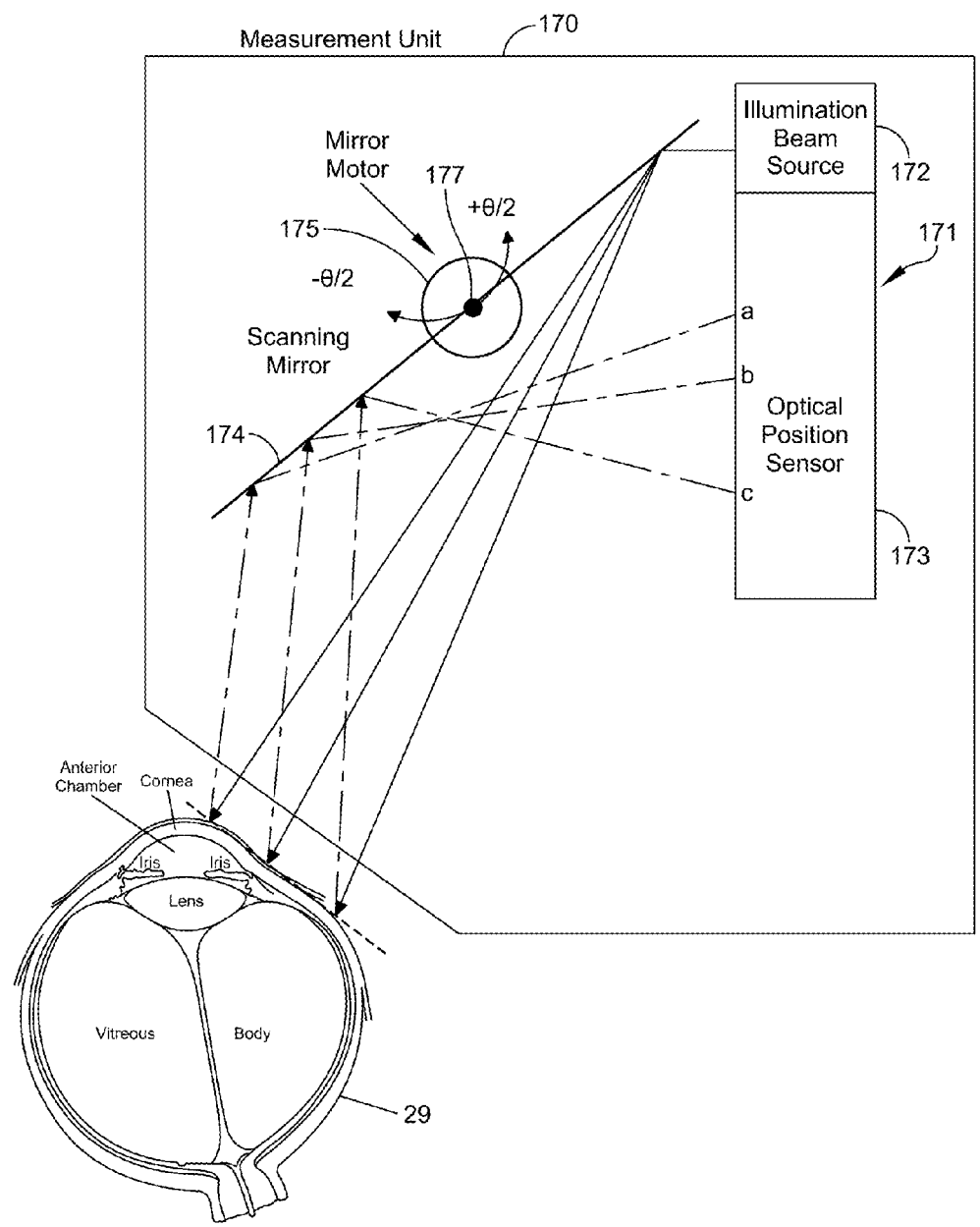
FIG. 24 depicts a seventh embodiment of apparatus incorporating this invention.

In FIG. 24 a measurement unit 170 includes a position sensor 171 with an integrated illumination source 172 and an optical position sensor 173. The illumination source 172 directs a beam to a scanning mirror 174 that a motor drive 175 oscillates about a narrow angular range (e.g., θ≈+/−5°). As this illumination beam scans a meridian across the eye, the reflected and scattered light from the eye 29 is directed toward the optical position sensor by scanning mirror 174 and is displaced on the position sensor, such as at points "a", "b" and "c" as scanning mirror 174 oscillates on a shaft 177 and corresponding axis. In FIG. 24 the long axis of the scanning mirror (shown as line 174) and the long axis of the integrated source beam-optical sensor triangulation unit are within the plane of the page. As the source beam scans the meridian along the tangent line, drawn in the plane of the page, the orientation of the optical position sensor within the triangulation unit and hence light rays corresponding to beams "a", "b" and "c" are also within the plane of the page. The imaging lens within the position sensor captures the lower magnitude out of plane light rays within the cone angle of the imaging optics The position sensor 161 in FIG. 23 and the position sensor 171 in FIG. 24 incorporate triangulation sensors that incorporate a structure and operation that processes the optical light rays based, in part, on the Schleimpflug theory, such as incorporated in the Micro Epsilon Model optoNCDT1700 BL series or optoNCDT2300 BL series, each of which incorporates a blue laser. The triangulation 161 and 171 may also include a red laser for some applications although a blue laser appears to provide better results when measuring biological material such as found in the eye.

Scanning mirror assemblies such as with scanning mirror 164 and mirror motor 165 in FIG. 23 and the scanning mirror 174 and motor 175 in FIG. 24 are available from Cambridge Technology and are repeatable to 10 micro-radians which is sufficient to provide a lateral resolution of 12 microns with scan speeds that permit a 20 to 40 millisecond radian scan time; i.e. the time to make one scan across the surface of the eye from about the top of the eye across the cornea and the entire sclera (over a scan of a meridian). Such a configuration can measure the distance to the cornea or sclera on eye 29, with a repeatability of 1 micron from 100 mm away. It has been found that the optical position sensor 163 in FIG. 23 picks up beams scattered to the side. In FIG. 24, the optical position sensor 173 picks up beams that are both reflected and scattered toward the sensor in the relative plane of the page. As a result, the position sensor 173 in FIG. 24 is less sensitive to signal degradation caused by variations in eye surface texture and angle.

Figure 25:
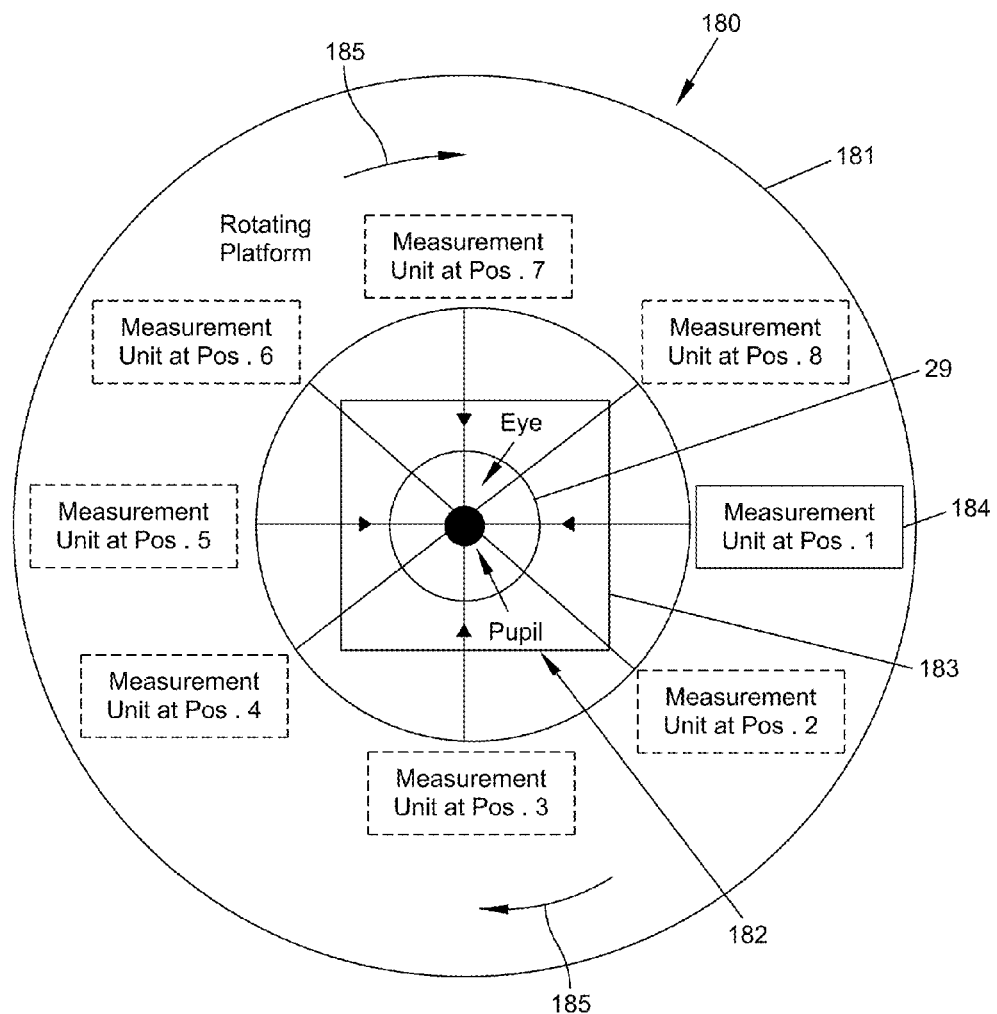
FIG. 25 is a schematic view that is useful in understanding this invention.
Figure 26:
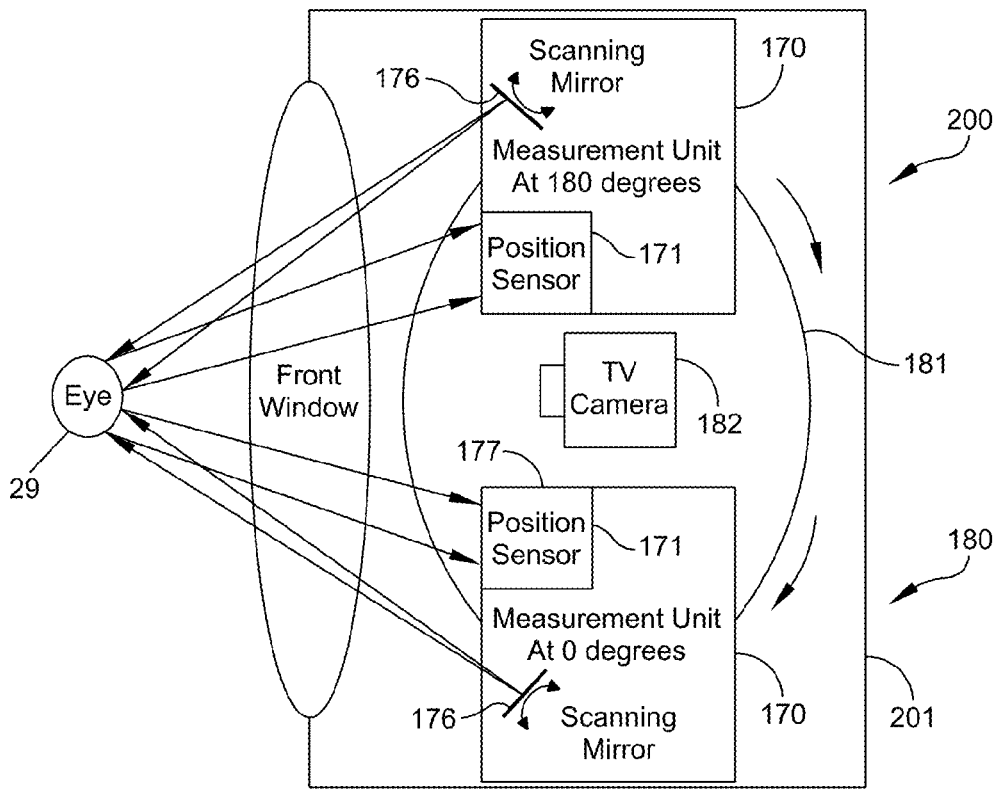
FIG. 26 is a block diagram of eye scanning apparatus constructed in accordance with this invention.

FIGS. 25 and 26 depict one embodiment of an eye-measuring apparatus 180 for obtaining a high-resolution three-dimensional image of the eye. This apparatus 180 includes a platform 181 that rotates about an axis that is substantially perpendicular to the optical axis of an eye 29 (parallel to the top front surface of the eye). Mounted on a fixed base (not shown) is a high-definition TV camera system 182 that monitors the patient's eye position within a region 183 during each scan and that has sufficient resolution to determine the position of the eye 29 relative to the position of a measurement unit 184 at different angular positions. More specifically, in one embodiment, the platform 181 rotates a single measurement unit, shown by solid lines 184 at a position 1, and dashed lines at other positions around a patient's eye. The angular motion of rotation is indicated by arrows 185 in FIG. 25. In this particular case the system in FIG. 25 depicts the measurement unit 184 at eight angular positions. As will be apparent, however, in practice the number of positions can be much greater to achieve necessary sampling during a single scan operation during which the platform rotates one revolution. It is expected that between 20 and 100 angular positions will be measured during the scanning operation for a single rotation of the platform 181 to achieve appropriate sampling for different applications and ophthalmic procedures.

As shown in FIG. 26, a physical embodiment 200 of apparatus incorporating this invention includes a housing 201 with a frame that defines fixed spatial relationships between the TV camera system 182 and the measurement unit 170 or any of the other measurement unit implementations. As previously indicated, the measurement unit 170 generates distance information corresponding to the distances between the internal reference position sensor 171 and the surface of the eye at a plurality of angular positions along each of a plurality of spaced scan lines during a scanning operation. In FIG. 26 the measurement unit 170 is shown at two different locations during its rotation with the platform 181 about an axis such as the viewing axis of the TV camera system 182. Rotation of the platform 181 is provided by a motor, typically a servo or stepping motor that is not shown but known in the art, to provide a series of angularly spaced scanning positions at each of which a single scan is taken. To obtain multiple scans during a scanning operation, the measurement unit 170 rotates about the eye and at each incremental position, defines a "meridian" along which the measurement unit 170 takes a meridian scan and obtains height information for that meridian.

Figure 27:
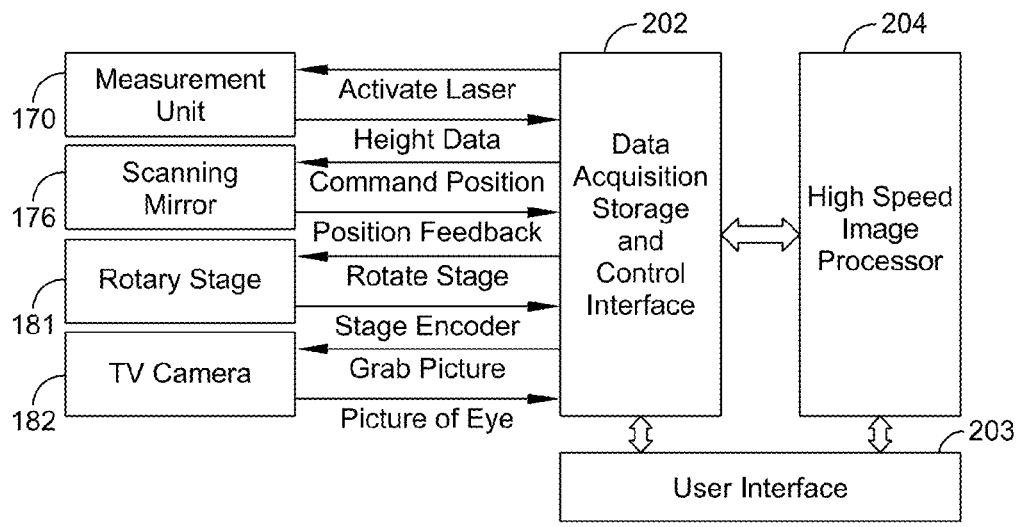
FIG. 27 is a schematic view of a control system that is useful with the eye scanning apparatus in FIG. 26.

FIG. 27 depicts one embodiment of a control system for the apparatus 200 in FIG. 26 for interacting with the measurement unit 170, a scanning rotary stage corresponding to the platform 181 in FIGS. 25 and 26 and the TV camera system 182. A data acquisition, storage and control interface unit 202 interacts with the measurement unit 170, scanning mirror 176, rotary stage, such as the platform 181, and TV camera system 182. More specifically, the data acquisition, storage and control interface 202 activates the illumination source in the measurement unit 170, such as a blue laser, the scanning mirror 176 and the position sensor in the measurement unit 170 thereby to retrieve height data generated from the corresponding optical position sensor including position data for each height measurement. The data acquisition, storage and control interface 202 also sends signals representing command positions to the scanning mirror 176 and receives position feedback signals to allow accurate control of the scanning mirror angular position. Signals from the data acquisition, storage and control interface 202 also control the operation of the motor driving the rotary stage platform 181 or like support and receives encoded stage position signals representing the actual position of the rotary platform 181.

The TV camera system 182 is constantly monitoring the patient's eye. Upon a signal from the data acquisition, storage and control interface 202, the video system "grabs" a picture of the eye and returns it to the data acquisition, storage and control interface 202. Interaction and operational control is provided through a user interface 203 that includes input and visual output capability and that interfaces with both the data acquisition, storage and control interface and a high speed image processor 204. The image processor 204 processes the height signals in combination with the image received from the TV camera to produce the topography of that portion of the eye that has been sampled during a single scan of the eye along a meridian and accumulates all the scan information made during one scanning operation.

Referring to FIG. 26, in some applications and prior to collecting data, a patient is instructed to look into the apparatus 200. A doctor or operator causes the system to store a high resolution image of the patient's eye using TV camera system 182. Such an image would include all the fine features and details in the iris, features in the scleral region such as blood vessels and the position and shape of the pupil. In addition, the physician or operator could identify a particular feature in the eye by various means to be used as a reference point. Then the system collects data along every meridian (i.e., eight equiangularly displaced meridians in FIG. 25). If the TV camera system detects any eye movement during any meridian acquisition cycle, the data for the cycle is ignored and the eye can be rescanned at that meridian once the eye stops moving. With short data acquisition cycles, in the order of 20 to 50 milliseconds or so, the system will produce a sequence of high resolution snapshots, one for each different position of the measurement module.

Each "snapshot" from the TV camera system will be accompanied by the corresponding meridian height measurement data that defines the topology of the eye along that scan line. That is, each meridian scan line, such as the line 210 in FIG. 28 will have its own unique picture, shows the meridian scan line between points A and B which extends from the cornea to the sclera 42, and the precise orientation of the meridian relative to all the features in the TV image of the eye. FIG. 29 is a graphical representation of the relationship of the height measurements (from the measurement apparatus) as a function of the radial distance along the surface of the eye corresponding to the angular position of the scanning mirror.

Figure 28:
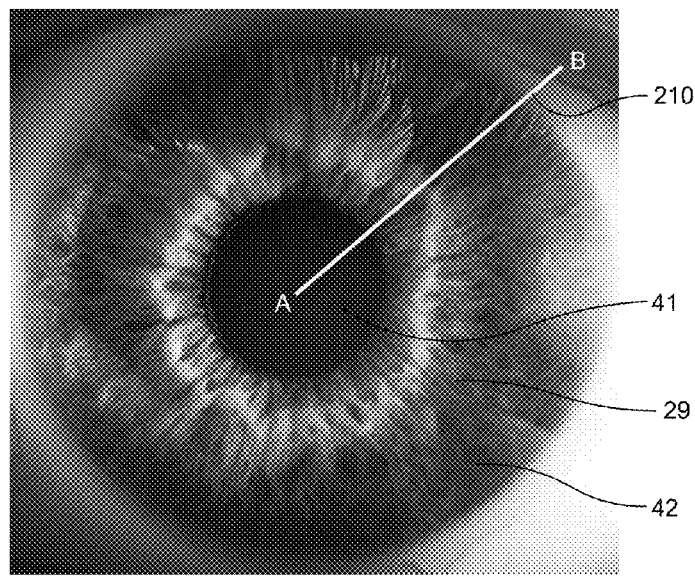
FIGS. 28, 29 and 30 are useful in understanding the generation of eye topography in accordance with one aspect of this invention.
Figure 29:
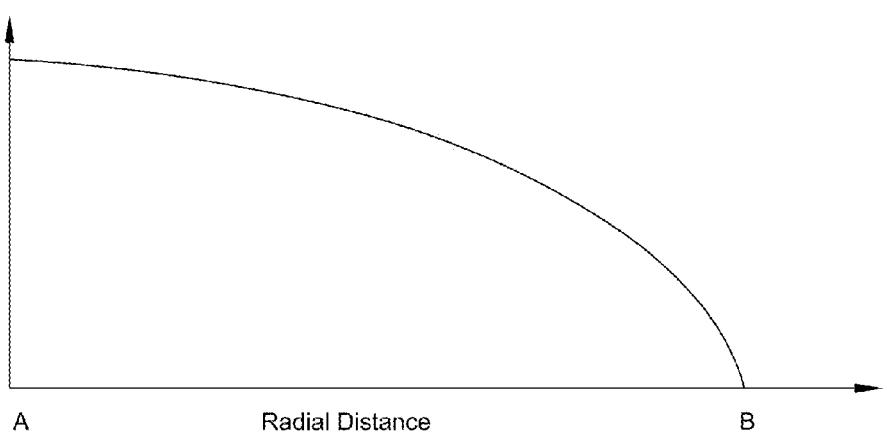
Figure 30:
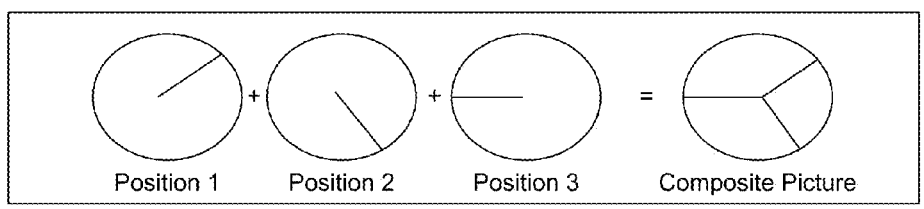

Once the measurement unit has rotated around the eye in a rotational scanning operation during which multiple meridian scans are obtained, a TV image similar to that of FIG. 28 and height measurement data similar to that of FIG. 29 will exist for each measured meridian. It is then possible to process and combine the data from all the meridians to produce an image of the eye for one orientation or starting position of the patient's eye. FIG. 30 graphically illustrates three such meridian scan operations for positions 1, 2 and 3, by way of example. The individual meridians, each consisting of a TV camera image with corresponding height measurement data can then be combined to produce a composite image for the rotational scanning operation. It has been found that such information can be processed by image-stitching software that overlays and superimposes each of the scans by stitching to spatially align the meridian data as shown in FIG. 30 for all the meridians in that scanning operation with the images of the eye in one orientation. Such composite images of the eye have been generated by the use of Autopano image-stitching software available from Kolor SARL of France.

Figure 31:
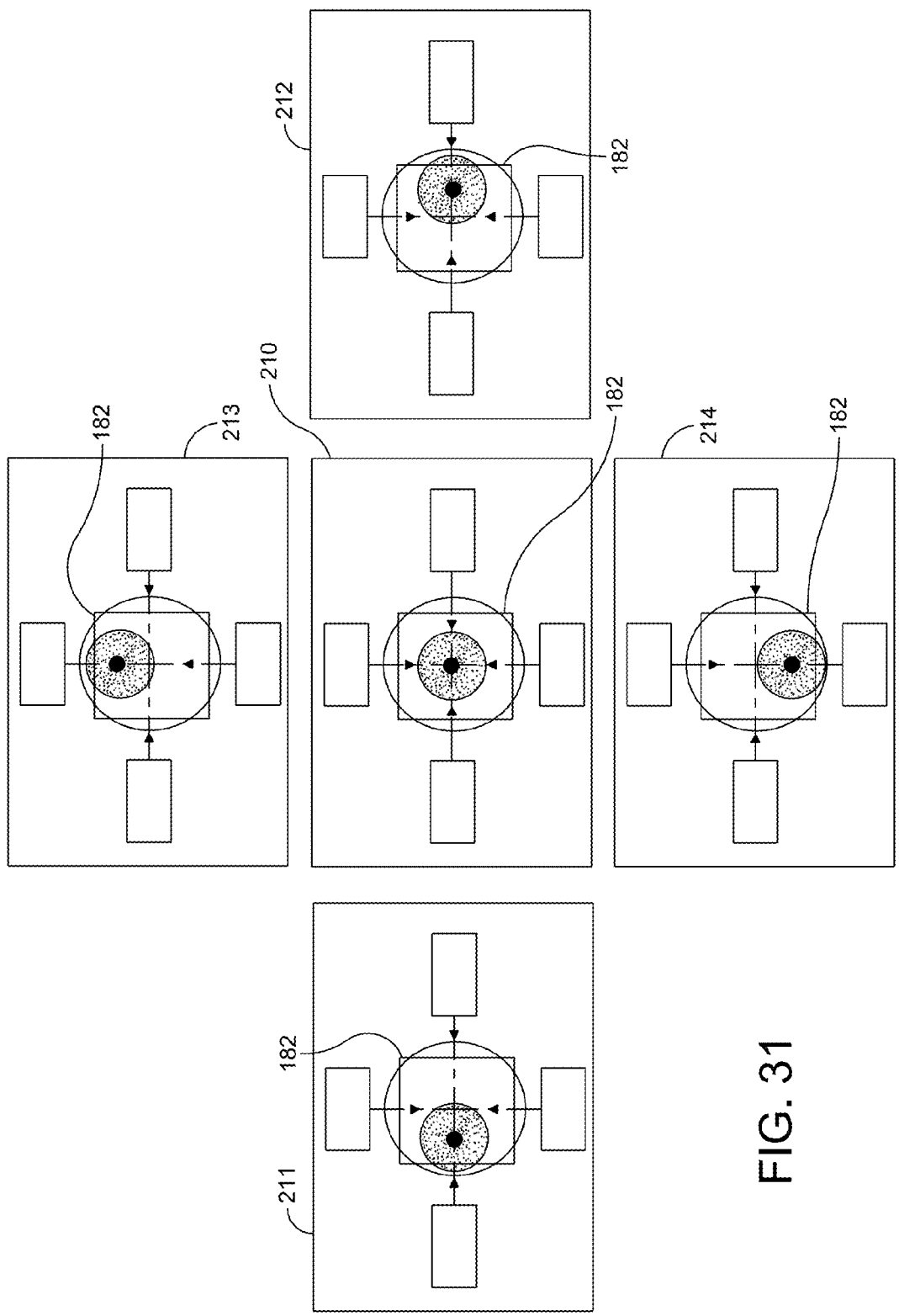
FIG. 31 is schematically depicts apparatus for obtaining a fully contoured model of the eye.

As previously stated, for a given orientation of an eye a portion of the sclera is covered by an eyelid. To scan the entire surface of the eye, including those regions normally covered by the eyelids different areas of a patient's eye can be scanned during a separate scanning operation for each of different orientations of the patient's eye. FIG. 31 discloses one approach in which a patient looks at a visual target sequentially projected to center, upper, lower, left, and right quadrants to expose the entire eye including the extreme anterior scleral surface. That is, a complete measurement of the eye includes five scanning operations, one for each of the eye positions at 210, 211, 212, 213 and 214. The scanning operation 210 occurs when the patient looking straight ahead. Each of the scanning operations at 211 and 212 occur when the patient looks to the right and left respectively; scanning operations 213 and 214 occur when the patient looks up and down respectively. Since the upper eyelid lowers as a patient looks down, a speculum may be used to hold the eyelids open. Alternatively, the eyelid can be taped to the patient's forehead prior to collecting data or held up by the patient's finger or the finger of a doctor. An alternate approach may avoid the need for taping the eyelids or using a speculum. Typically a patient will be scanned with the patient's chin on a chin rest or like positioning structure so that the patient's head remains reasonably fixed. Such devices are known in the art. However, rather than projecting a target for viewing and aligning as previously described, a single target can be projected and then the patient can angularly rotate his or her head a small amount (e.g. about ±15°). The eye will naturally rotate to a new position as shown in FIG. 31 as the patient's head moves to keep the fixed target image in view.

Figure 32:
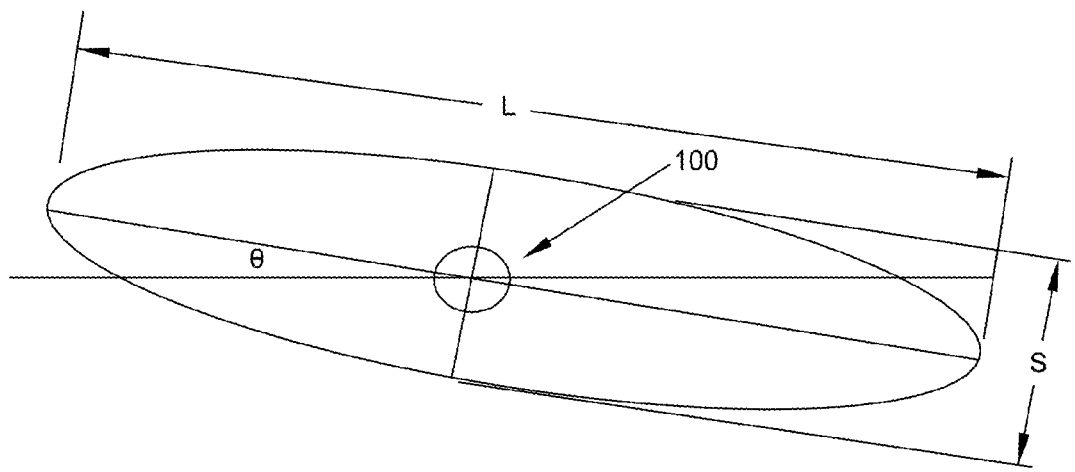
FIG. 32 is useful in understanding toricity of the eye.

By whatever means is used to obtain the images from multiple scanning operations at different eye orientations, it is possible to process the data for each scanning operation and stitch the data together to create a three-dimensional wide-field topology map of the eye using the above-identified Kolor Autopano or like software. In addition, the human eye is often toric in shape, like a foot ball, having two base curves, with a longer axis and a shorter axis, as shown in FIG. 32. The goal is to design a lens that matches this ocular surface, but this is difficult by conventional means because the scleral lens sits under the upper and lower eyelids. Toricity of the bearing surface can only be calculated after aligning and stitching together all meridians or cross sectional data as previously described.

Figure 33:
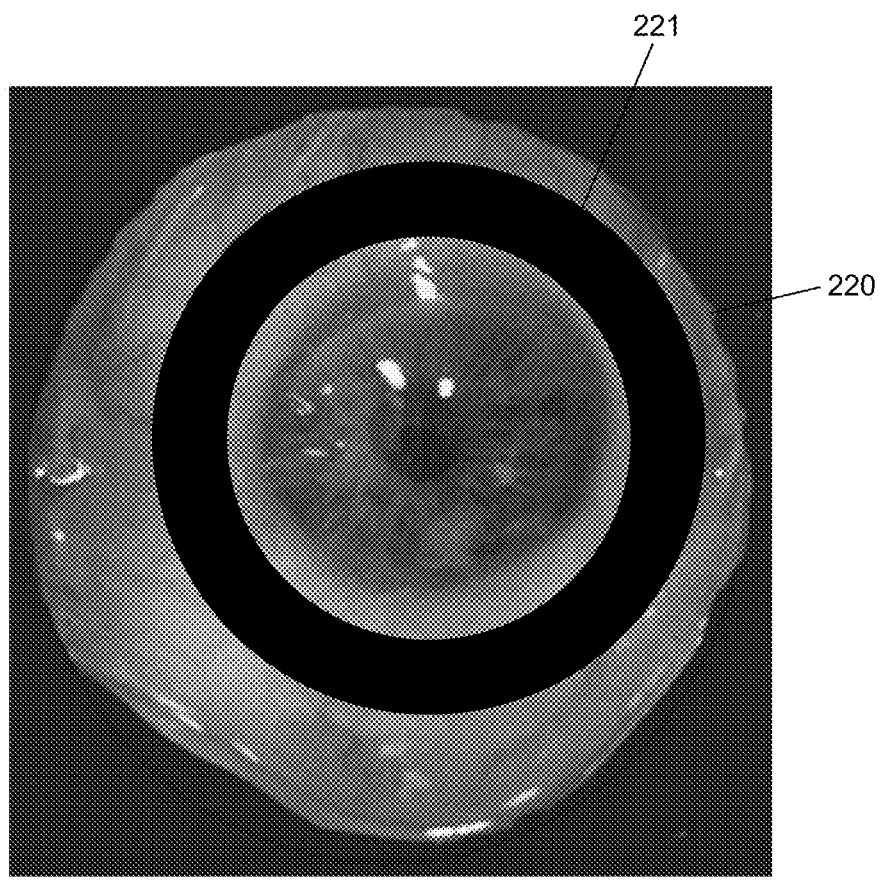
FIG. 33 is an example of an image of an eye obtained in accordance with certain aspects of this invention as might be used by an ophthalmologist.

FIG. 33 shows the information presentation that can be derived from this methodology using such stitching software. Multiple images of an individual's eye were taken with a TV camera and then stitched together. The result is the composite image 220 of the individual's eye. This image is a graphical presentation of all the accumulated data from a set of scanning operations. The ring 221 represents a template which has been manipulated on the image of FIG. 33 to define the boundaries of an area of the sclera for supporting a sclera lens. Using conventional techniques a physician can manipulate the template of the ring to custom align the ring taking into account physical features of an eye. That information can be processed along the all the scan data to obtain a model from which a sclera lens for that patient can be constructed efficiently.

Figure 34:
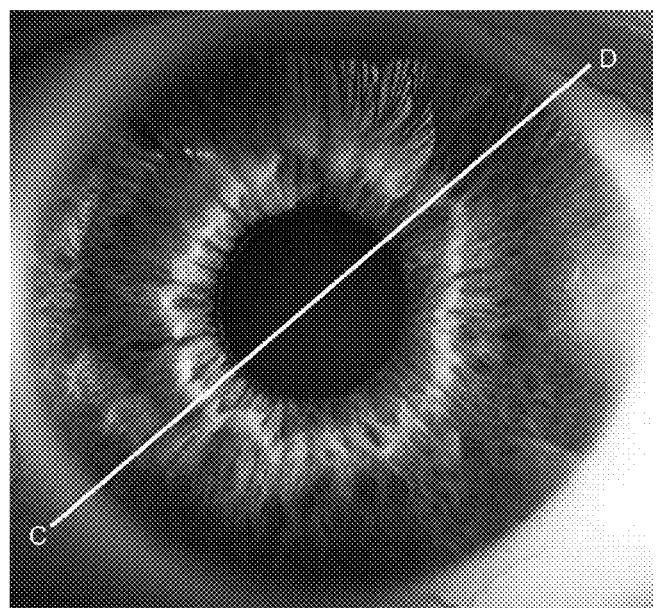
FIGS. 34 and 35 are images of an eye and the range of coverage obtained with OCT apparatus.
Figure 35:
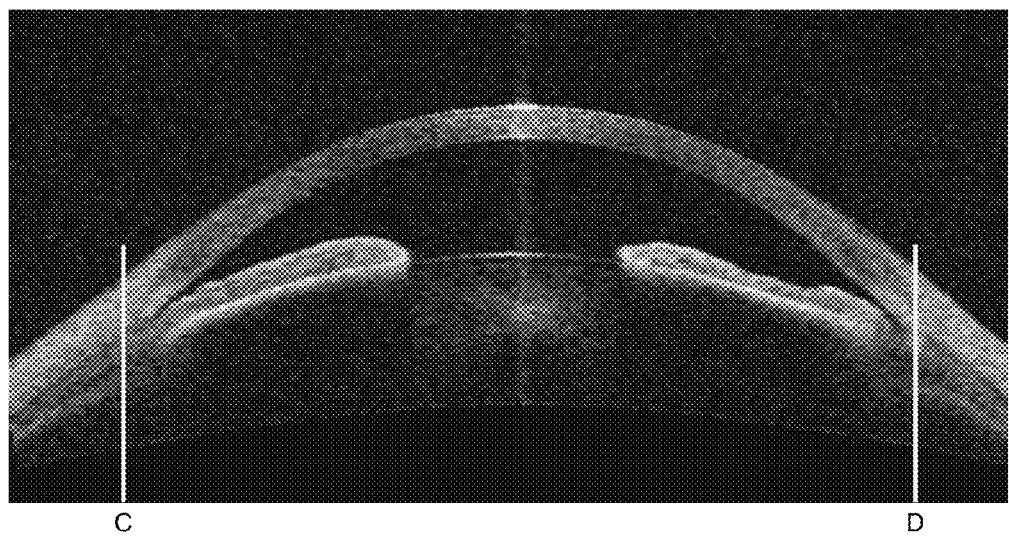
Figure 36:
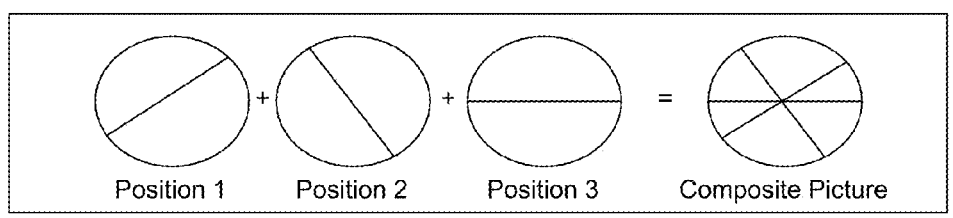
FIG. 36 is an example of how an OCT system can be modified to obtain greater coverage of the eye.
Figure 37A:
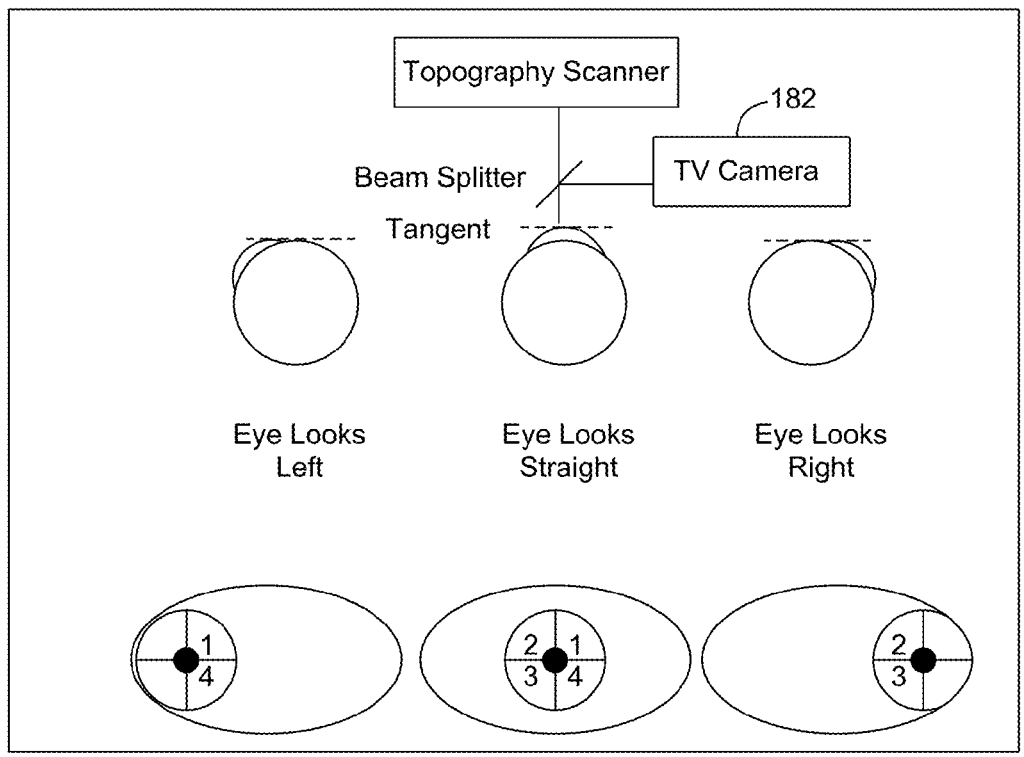
FIGS. 37A and 37B are helpful in understanding apparatus that might be used to extend the effectiveness of OCT apparatus.
Figure 37B:
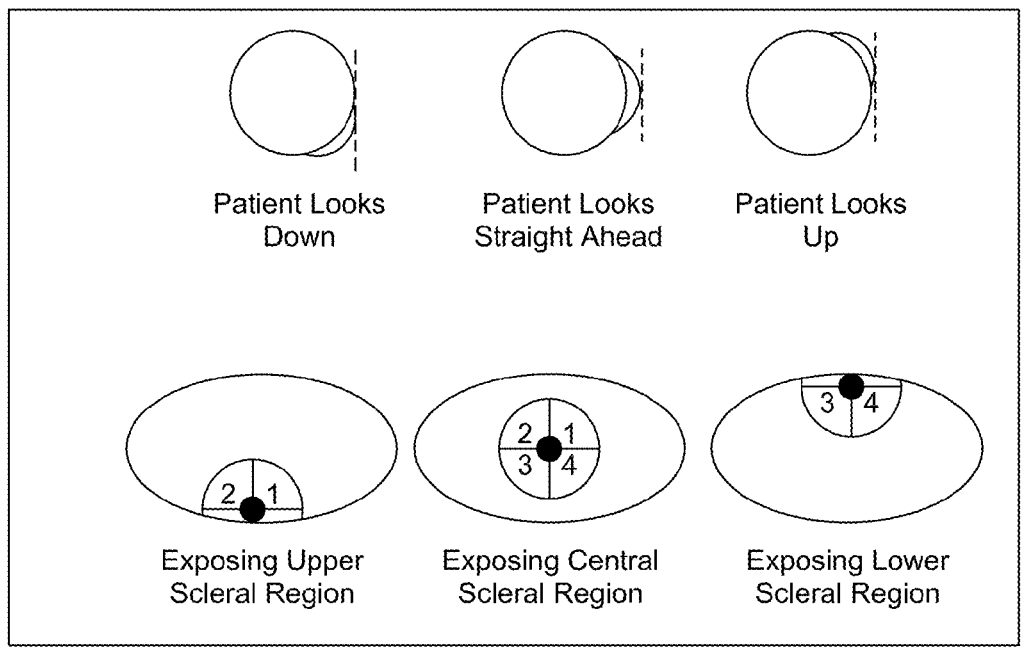

As previously indicated, OCT scanners have been shown to be limited in their ability to scan highly curved surfaces such as the sclera and need to be positioned relatively perpendicular to the top corneal surface. FIG. 34 depicts the image of an eye with a superimposed diameter line C-D which corresponds to the extent of the OCT image shown in FIG. 35 between the limits C and D. In the configuration shown in FIGS. 37A and 37B, the topology scanner can either be a meridian scanner as described above or a conventional OCT type cross sectional scanner with an output as shown in FIG. 35. FIGS. 37A and 37B illustrate a scanner configuration with an orientation close to perpendicular relative to the top corneal surface. In this configuration the scanner tangent line is oriented at a shallow angle relative to the top surface of the cornea. As the eye rotates and fixates at different angular positions, different regions of the eye become almost parallel with the tangent line and fall within the angular range of the topology scanner. For each position of the eyeball multiple meridians or cross sections are scanned. Each scanned meridian or cross section is accompanied by a TV camera image. TV images with corresponding meridian height data for the different positions of the eye are then aligned to combine and reference all meridians or cross sections to a fixed reference points in the eye to create a 3 dimensional model of the eye. FIG. 34 shows the camera picture of an eye and the angular orientation of an OCT radial scan line, indicated by line C-D. FIG. 35 is the OCT image for radial scan line C-D. FIG. 36 illustrates how successive and multiple OCT scans are combined using the same procedure previously described to combine meridian data.

Each of the foregoing embodiments of this invention meets some or all of the various objectives of this invention. That is, the method and apparatus described above provide accurate measurements of the topography of the eye, especially of the topography of the corneal, scleral and limbus regions of the eye taking into account the toricity of the scleral and corneal region. As a result, the method and apparatus of this invention can assist in minimizing and simplifying the effort for making scleral contact lenses by minimizing and simplifying the process for determining the topography of the eye, particularly the topography of the corneal and scleral regions of an eye including the measurement of the toricity of the sclera and eye automatically, for computing the long and short toric axes automatically, for scanning the eye automatically to provide profile information along the two toric axes, and to create an accurate three-dimensional model of the eye. The apparatus is also useful in Lasik and cataract ophthalmic procedures to provide accurate topology data of the corneal region.

This invention has been disclosed in terms of certain embodiments. It will be apparent that many modifications can be made to the disclosed apparatus without departing from the invention. For example, an OCT scanner might be modified by certain aspects of the invention. FIG. 35 shows a full cross sectional image of an eye created by an OCT scanner. As shown, it includes the cornea and very top of the sclera near the Limbus but it does not show the steep regions of the sclera past the Limbus. Insertion of a beam splitter or dichroic mirror into the optical path as shown in FIG. 37A enables the TV camera 182 to be offset so the optical beams from the scanner and camera are both oriented perpendicular to the top of the corneal surface, as the eye looks straight. In addition, when the viewing angles of the TV camera become close to the beam angles of the meridian or cross section in an OCT scanner, insertion of a beam splitter or dichroic mirror into the optical path can avoid mechanical interference between the two units. If the measurement unit uses a monochromatic light source such as a blue beam for example or a source outside the visible spectrum such as the near IR wavelengths used in numerous OCT units the beam splitter can be replaced with a dichroic mirror to maximize power to the topology scanner and TV camera. Therefore, it is the object of the claims to cover all such variations and modifications as come within the true spirit and scope of this invention.

What is claimed is:

1. Apparatus for generating a three-dimensional topography of a surface of an eye characterized by a distinct visual feature, said apparatus comprising:
    A) a camera mounted on a fixed base and directed along an imaging axis for generating a sequence of two-dimensional images of the eye including the distinct visual feature,
    B) a scanner that generates distance information corresponding to distances from an internal reference of the apparatus to the surface of the eye at a plurality of positions along a meridian scan line during a meridian scanning operation,
    C) a rotary stage for rotating said scanner to a plurality of angular positions, to thereby also rotate an angular position of the meridian scan line, the rotary stage disposed at a determined physical spacing with respect to the fixed base, to thereby also place the camera at a determined physical spacing with respect to the scanner for each of the plurality of angular positions, and
    D) a control connected to said camera, said rotary stage and said scanner, said control:
        i) configured to control said scanner to produce a plurality of distance measurements along each meridian scan line for a plurality of meridian scanning operations, a corresponding meridian scanning operation performed for each of the plurality of angular positions of the rotary stage,
        ii) configured to capture a two-dimensional image of the eye generated by the camera simultaneously with each meridian scanning operation, thereby capturing a corresponding two-dimensional image simultaneously with each meridian scan line,
        iii) configured to store the distance measurements obtained along each meridian scan line and its corresponding two-dimensional image captured during each meridian scanning operation, and
    E) an image processor configured to process the stored distance measurements and the corresponding simultaneously captured two-dimensional images to thereby align the two-dimensional images to obtain a composite three-dimensional image of the eye corresponding to the three-dimensional topography of the eye surface and thereby compensate for eye motion during the plurality of meridian scanning operations.

2. Apparatus as recited in claim 1 wherein said scanner comprises a measurement unit having an illumination source and imaging means for receiving light reflected from the eye surface and producing distance measurements for each meridian scan.

3. Apparatus as recited in claim 2 wherein during each meridian scan distance measurements are made for at least one of a cornea and of a sclera of the eye.

4. Apparatus as recited in claim 1 wherein said scanner comprises a measurement unit having an optical position sensor with an illumination source and having a scanning mirror that, during each meridian scan, directs illumination from said illumination source across a portion of the eye.

5. Apparatus as recited in claim 1 additionally comprising visual target means for providing a visual target for the patient to view thereby to fix an orientation of the eye for each angular position of the rotary stage.

6. Apparatus as recited in claim 5 wherein said visual target means includes means for changing a position of a patient's head thereby to induce motion of the eye to expose different regions of the eye for each rotational scanning operation.

7. Apparatus for generating a three-dimensional topography of a portion of a surface of an eye, the surface including one or more of a surface of a cornea, a surface of a sclera, or a surface including both the cornea and sclera, the surface characterized by a distinct visual feature, the apparatus comprising:
   A) a camera directed along an imaging axis for generating a sequence of two-dimensional images of the eye including the distinct visual feature, the camera mounted on a fixed base,
   B) a scanner that generates a plurality of distance measurements corresponding to distances from an internal reference to the surface of the eye at a plurality of positions along a meridian scan line during a meridian scanning operation,
   C) a platform, rotatable about the imaging axis to a plurality of different angular positions, on which is disposed the scanner, the platform disposed at a determined distance from the fixed base, to thereby arrange the scanner with a determined physical spacing with respect to the camera, and
   D) a control connected to said camera and said scanner, the control:
      i) controlling the scanner to produce a plurality of height measurements from the plurality of distance measurements using triangulation at different positions during each one of a plurality of meridian scanning operations,
      ii) capturing a two-dimensional image of the eye from the camera simultaneously with each one of the plurality of meridian scanning operations, thereby capturing a corresponding simultaneous image with each meridian scanning operation,
      iii) rotating an angular position of the platform to arrange the scanner to a plurality of angular positions,
      iv) storing the plurality of height measurements obtained by the scanner and the corresponding captured two-dimensional image from the camera for each meridian scanning operation and for each angular position of the platform, and
      v) processing the height measurements and the corresponding simultaneously captured two-dimensional images for each angular position to align the captured images and to align the plurality of height measurements, to thereby generate a composite three-dimensional topography of the eye, and to thereby compensate for movement of the eye during the plurality of meridian scanning operations.

8. Apparatus as recited in claim 7 wherein said scanner comprises a measurement unit having an illumination source and having imaging means for receiving light from the eye surface and producing height distances for the scan.

9. Apparatus as recited in claim 8 wherein said measurement unit is positioned relative to the eye whereby a scan measures distances to at least one of the cornea and sclera of the eye.

10. Apparatus as recited in claim 7 wherein said scanner comprises a measurement unit having an optical position sensor with an illumination source and having a scanning mirror that, during a scan, directs illumination from said illumination source across a portion of the eye thereby to define the scan.

11. Apparatus as recited in claim 7 wherein said scanner comprises an optical coherence tomography scanner.

12. Apparatus as recited in claim 11 wherein the control is further for processing the output of the optical coherence tomography scanner to obtain the distance measurement information.

13. Apparatus as recited in claim 7 wherein the control further obtains the three-dimensional topography of at least one of the cornea, the sclera, or the cornea and sclera based upon the output of the optical coherence tomography scanner.

14. Apparatus as recited in claim 7 wherein the scanner uses triangulation to obtain the plurality of height measurements.

15. Apparatus as recited in claim 7 wherein an axis of an incident scanning beam produced by the scanner intersects a line tangent to both a first point on the surface of the cornea and a second point on the surface of the sclera.

16. Apparatus as recited in claim 15 wherein during each meridian scanning operation, height measurements are made to the cornea or the sclera or the cornea and the sclera.

17. Apparatus as recited in claim 15 wherein when the angular position of the platform is rotated to two different determined positions, the incident scanning beam intersects a first tangent line and a second tangent line, the first and second tangent lines located on opposite sides of the eye.

18. Apparatus for generating a three-dimensional topography of a portion of a surface of an eye, the surface including one or more of a surface of a cornea, a surface of a sclera, or a surface including both the cornea and sclera, the surface—characterized by a distinct visual feature, the apparatus comprising:
   A) a camera directed along an imaging axis for generating a sequence of two-dimensional images of the eye including the distinct visual feature,
   B) a scanner that generates distance information corresponding to distances from an internal reference to the surface of the eye at a plurality of positions along a meridian scan line during a meridian scanning operation,
   D) a control connected to said camera and said scanner, the control:
      i) controlling the scanner to produce a plurality of height measurements at different positions during a plurality of meridian scanning operations,
      ii) capturing an image of the eye from the camera during each of the plurality of meridian scans, thereby capturing a corresponding image for each meridian scanning operation,
      iii) obtaining a meridian scan for each of a plurality of fixed positions of the scanner with respect to the camera,
      iv) storing the plurality of height measurements obtained by the scanner and the corresponding captured image information from the camera for each meridian scanning operation and for each position, and
      v) processing the distance measurement information and the corresponding captured images to align the captured images, to thereby generate a composite three dimensional image of the eye, and to thereby also obtain the three-dimensional topography, and to thereby compensate for movement of the eye during the plurality of meridian scanning operations.

* * * * *